(12) United States Patent
Rosenberg et al.

(10) Patent No.: US 8,038,653 B2
(45) Date of Patent: Oct. 18, 2011

(54) ANCHOR SYSTEMS AND METHODS

(75) Inventors: Michael Rosenberg, Eagan, MN (US); Mark R. Christianson, Plymouth, MN (US); Kyle P. Taylor, Brooklyn Park, MN (US); Andrew T. Forsberg, Minneapolis, MN (US); Jeffrey D. Killion, Plymouth, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 212 days.

(21) Appl. No.: 12/174,306

(22) Filed: Jul. 16, 2008

(65) Prior Publication Data
US 2010/0016801 A1 Jan. 21, 2010

(51) Int. Cl.
*A61M 5/32* (2006.01)
*A61F 11/00* (2006.01)

(52) U.S. Cl. .................. 604/174; 604/180; 606/108

(58) Field of Classification Search .................. 604/174, 604/180, 179; 606/108
See application file for complete search history.

(56) References Cited

U.S. PATENT DOCUMENTS

| | | | |
|---|---|---|---|
| 2,525,398 A | 10/1950 | Collins | |
| 3,039,468 A | 6/1962 | Price | |
| 3,059,645 A | 10/1962 | Hasbrouck et al. | |
| 3,108,595 A | 10/1963 | Overment | |
| 3,176,690 A | 4/1965 | H'Doubler | |
| 3,308,819 A | 3/1967 | Arp | |
| 3,630,195 A | 12/1971 | Santomieri | |
| 3,677,250 A | 7/1972 | Thomas | |
| 3,717,151 A | 2/1973 | Collett | |
| 3,765,032 A | 10/1973 | Palma | |
| 3,834,380 A | 9/1974 | Boyd | |
| 3,856,009 A | 12/1974 | Winnie | |
| 3,896,527 A | 7/1975 | Miller et al. | |
| 3,938,529 A | 2/1976 | Gibbons | |
| 4,043,346 A | 8/1977 | Mobley et al. | |
| 4,114,618 A | 9/1978 | Vargas | |
| 4,164,943 A | 8/1979 | Hill et al. | |
| 4,248,224 A | 2/1981 | Jones | |
| 4,309,994 A | 1/1982 | Grunwald | |
| 4,397,647 A | 8/1983 | Gordon | |
| 4,474,569 A | 10/1984 | Newkirk | |
| 4,569,344 A | 2/1986 | Palmer | |
| 4,592,356 A | 6/1986 | Gutierrez | |
| 4,645,492 A | 2/1987 | Weeks | |

(Continued)

FOREIGN PATENT DOCUMENTS
WO    WO 91/15254    10/1991
(Continued)

OTHER PUBLICATIONS

International Search Report & Written Opinion, PCT/US2009/048500, mailed Jan. 25, 2010, 12 pages.

(Continued)

*Primary Examiner* — Theodore Stigell
*Assistant Examiner* — Imani Hayman
(74) *Attorney, Agent, or Firm* — Fish & Richardson P.C.

(57) ABSTRACT

Some embodiments of a medical device anchor system include an anchor device that receives a medical instrument (such as a catheter or the like) and secures the instrument in place relative to a skin penetration point. In some circumstances, the anchor device may allow the anchor device to be used after medical instrument is already in place without the need for a second penetration point for the anchor device.

33 Claims, 20 Drawing Sheets

U.S. PATENT DOCUMENTS

| | | |
|---|---|---|
| 4,665,906 A | 5/1987 | Jervis |
| 4,799,495 A | 1/1989 | Hawkins et al. |
| 4,804,359 A | 2/1989 | Grunwald et al. |
| 4,813,930 A | 3/1989 | Elliott |
| 4,936,823 A | 6/1990 | Colvin et al. |
| 4,986,810 A | 1/1991 | Semrad |
| 5,041,085 A | 8/1991 | Osborne et al. |
| 5,067,957 A | 11/1991 | Jervis |
| 5,122,122 A | 6/1992 | Allgood |
| 5,190,546 A | 3/1993 | Jervis |
| 5,256,146 A | 10/1993 | Ensminger et al. |
| 5,267,960 A | 12/1993 | Hayman et al. |
| 5,279,564 A | 1/1994 | Taylor |
| 5,312,337 A | 5/1994 | Flaherty et al. |
| 5,344,439 A | 9/1994 | Otten |
| 5,368,017 A | 11/1994 | Sorenson et al. |
| 5,378,239 A | 1/1995 | Termin et al. |
| 5,456,671 A | 10/1995 | Bierman |
| 5,496,277 A | 3/1996 | Termin et al. |
| 5,540,648 A | 7/1996 | Yoon |
| 5,578,013 A | 11/1996 | Bierman |
| 5,597,378 A | 1/1997 | Jervis |
| 5,599,311 A | 2/1997 | Raulerson |
| 5,653,718 A | 8/1997 | Yoon |
| 5,681,288 A | 10/1997 | Schlitt |
| 5,688,247 A | 11/1997 | Haindl et al. |
| 5,702,371 A | 12/1997 | Bierman |
| 5,707,362 A | 1/1998 | Yoon |
| 5,722,959 A | 3/1998 | Bierman |
| 5,728,133 A | 3/1998 | Kontos |
| 5,741,234 A | 4/1998 | Aboul-Hosn |
| 5,746,720 A | 5/1998 | Stouder, Jr. |
| 5,755,697 A | 5/1998 | Jones et al. |
| 5,769,821 A | 6/1998 | Abrahamson et al. |
| 5,800,402 A | 9/1998 | Bierman |
| 5,810,781 A | 9/1998 | Bierman |
| 5,814,065 A | 9/1998 | Diaz |
| 5,827,230 A | 10/1998 | Bierman |
| 5,833,664 A | 11/1998 | Seare, Jr. |
| 5,833,667 A | 11/1998 | Bierman |
| 5,857,999 A | 1/1999 | Quick et al. |
| 5,921,965 A | 7/1999 | Blei |
| 5,928,266 A | 7/1999 | Kontos |
| 5,944,732 A | 8/1999 | Raulerson et al. |
| 5,947,931 A | 9/1999 | Bierman |
| 5,971,960 A | 10/1999 | Flom et al. |
| 5,989,265 A | 11/1999 | Bouquet De La Joliniere et al. |
| 6,213,979 B1 | 4/2001 | Bierman |
| 6,290,676 B1 | 9/2001 | Bierman |
| 6,413,240 B1 | 7/2002 | Bierman et al. |
| 6,447,485 B2 | 9/2002 | Bierman |
| 6,540,693 B2 | 4/2003 | Burbank et al. |
| 6,572,588 B1 | 6/2003 | Bierman et al. |
| 6,582,388 B1 | 6/2003 | Coleman et al. |
| 6,582,403 B1 | 6/2003 | Bierman et al. |
| 6,663,600 B2 | 12/2003 | Bierman et al. |
| 6,679,851 B2 | 1/2004 | Burbank et al. |
| 6,695,861 B1 | 2/2004 | Rosenberg et al. |
| 6,770,055 B2 | 8/2004 | Bierman et al. |
| 6,896,665 B2 | 5/2005 | Picha et al. |
| 6,958,044 B2 | 10/2005 | Burbank et al. |
| 7,056,286 B2 | 6/2006 | Ravenscroft et al. |
| 2002/0068898 A1 | 6/2002 | McGucklin, Jr. et al. |
| 2002/0068899 A1 | 6/2002 | McGucklin, Jr. et al. |
| 2002/0120250 A1 | 8/2002 | Altman |
| 2002/0165489 A1 | 11/2002 | McGucklin, Jr. et al. |
| 2005/0187578 A1 | 8/2005 | Rosenberg et al. |
| 2005/0256458 A1 | 11/2005 | Howard et al. |
| 2007/0021685 A1 | 1/2007 | Oepen et al. |
| 2007/0078397 A1* | 4/2007 | Weststrate ............... 604/164.01 |
| 2007/0225651 A1 | 9/2007 | Rosenberg et al. |
| 2007/0232997 A1 | 10/2007 | Glenn |
| 2008/0312599 A1 | 12/2008 | Rosenberg |
| 2009/0099527 A1 | 4/2009 | Rosenberg et al. |
| 2009/0326473 A1 | 12/2009 | Rosenberg et al. |

FOREIGN PATENT DOCUMENTS

| | | |
|---|---|---|
| WO | WO 2004/026152 | 4/2004 |
| WO | WO 2005/039419 | 5/2005 |
| WO | WO 2005/102438 | 11/2005 |

OTHER PUBLICATIONS

U.S. Appl. No. 60/412,453, filed Sep. 20, 2002, Claude et al.

Johnson & Johnson web page printout, "The EndoANCHOR Features and Benefits" printed Sep. 13, 2005, 2 pages.

Johnson & Johnson web page printout, "The EndoANCHOR Firing Sequences" printed Sep. 13, 2005, 2 pages.

Johnson & Johnson web page printout, "The EndoANCHOR Comparative Summary" printed Sep. 13, 2005, 2 pages.

Web Page Printout of Statlock Device, author and date unknown.

European Patent Office, European Search Report and Written Opinion for European Application No. EP 09798524, dated Jul. 4, 2011, 6 pages.

\* cited by examiner

ANCHOR SYSTEMS AND METHODS

TECHNICAL FIELD

This document relates to an anchor device, such as a device for use in securing the position of a catheter or other medical instrument.

BACKGROUND

Venous, arterial, and body fluid catheters are commonly used by physicians. For example, such catheters may be used to gain access to the vascular system for dialysis, for introducing pharmaceutical agents, for nutrition or fluids, for hemodynamic monitoring, and for blood draws. Alternatively, catheters can be used for drainage of fluid collections and to treat infection. Following introduction into the patient, the catheter is secured to the patient. In conventional practice, the catheter is commonly secured to the patient using an adhesive tape on the skin or by suturing a catheter hub to the patient's skin.

SUMMARY

Some embodiments of a medical device anchor system include an anchor device that receives a medical instrument (such as a catheter or the like) and secures the instrument in place relative to a skin penetration point. In some circumstances, the anchor device can be actuated so that subcutaneous anchors are inserted through the skin penetration point that is already occupied by the medical instrument. Such a configuration may allow the anchor device to be used after medical instrument is already in place without the need for a second penetration point for the anchor device. In particular embodiments, the anchor device may have a multi-piece design that can simplify removal of the device and reduce trauma to surrounding tissue near the penetration point. For example, the anchor device can be separated into at least two portions prior to removal from the skin penetration point. In these circumstances, the separable portions may include a subcutaneous anchor, and each anchor can be removed from the skin penetration point independently of the other in a manner that reduces the likelihood of damage to the tissue surrounding the skin penetration point.

Particular embodiments may include an anchor system for securing a medical instrument. The system may include a retainer body to couple to a catheter. The system may also include a plurality of flexible anchors releasably coupled to the retainer body. Each anchor may comprise a flexible tine that is deployable in a subcutaneous region to secure the retainer body relative to a penetration point. The system may further include an actuator that, when activated, moves the anchors from a non-deployed position to a deployed position in which the anchors flexible anchors extend distally from the retainer body and into the subcutaneous region.

In some embodiments, an anchor system for securing a medical instrument may include a retainer body to couple with a medical instrument. The system may also include one or more anchors that are deployable through a penetration point and into subcutaneous region so as to secure the retainer body relative to the penetration point. The system may further include a separable delivery device including an actuator that, when activated, moves the first and second anchors from a non-deployed position to a deployed position in which the anchors flexible anchors extend distally from the retainer body and into the subcutaneous region. The system may also include a release member that releasably couples the first and second anchors to the retainer body. The release member may be adjustable from a first position to a second position in which the first and second anchors are decoupled from the retainer body.

In other embodiments, a method of anchoring a catheter may include advancing a catheter through a skin penetration point. The method may also include directing an anchor device toward the skin penetration point that is occupied by a portion of the catheter. The anchor device may comprise a retainer body to releasably couple to an external portion of the catheter arranged outside of a biological body, and at least one deployable anchor that is longitudinally adjustable relative to the retainer body from a non-deployed position to a deployed position in which the at least one anchor extends distally from the retainer body. The method may further include deploying the anchor through the penetration point that is occupied by the catheter so that at least a portion of the anchor is deployed in a subcutaneous region proximate the penetration point.

These and other embodiments may provide one or more of the following advantages. First, some embodiments of an anchor system can retain a medical instrument in a desired position relative to a skin penetration point without necessarily requiring sutures or skin adhesives. Second, in some embodiments, an anchor device can include a retention portion that readily mates with a medical instrument (such as a catheter) and at least one anchor extending distally from the retention portion to engage the skin penetration point as the medical instrument. Third, the anchor device can include one or more anchors configured to deploy in a subcutaneous region under the skin proximate to the skin penetration point of the medical instrument. In such circumstances, the anchors may be inserted through the skin penetration point in a manner that reduces the likelihood of trauma to the surround skin tissue. Fourth, in some embodiments, the anchor device may include multiple components that are separable from one another before the anchor device is removed from the skin. For example, the anchor device may include a first portion and a second portion that are coupled together (as the fully assembled anchor device) during insertion into the skin penetration point, but the first and second portions can be readily separated from one another to facilitate removal from the skin. Accordingly, the anchors and associated tines can collectively penetrate into the subcutaneous region as part of the assembled device, and may be separately and individually withdrawn from the penetration point during the removal process. Such a configuration can permit the first and second portions to be maneuvered in a manner that reduces the likelihood of causing damage to the skin during removal of the anchors. Fifth, some embodiments of the anchor device may include a delivery device that facilitates delivery of the anchors toward the skin penetration point. For example, the delivery device may be configured as a disposable, hand-held actuator that provides for convenient grasping by a user. Moreover, the delivery device can be actuated so as to deploy the anchors into the subcutaneous region before the delivery device is removed from the anchor device.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
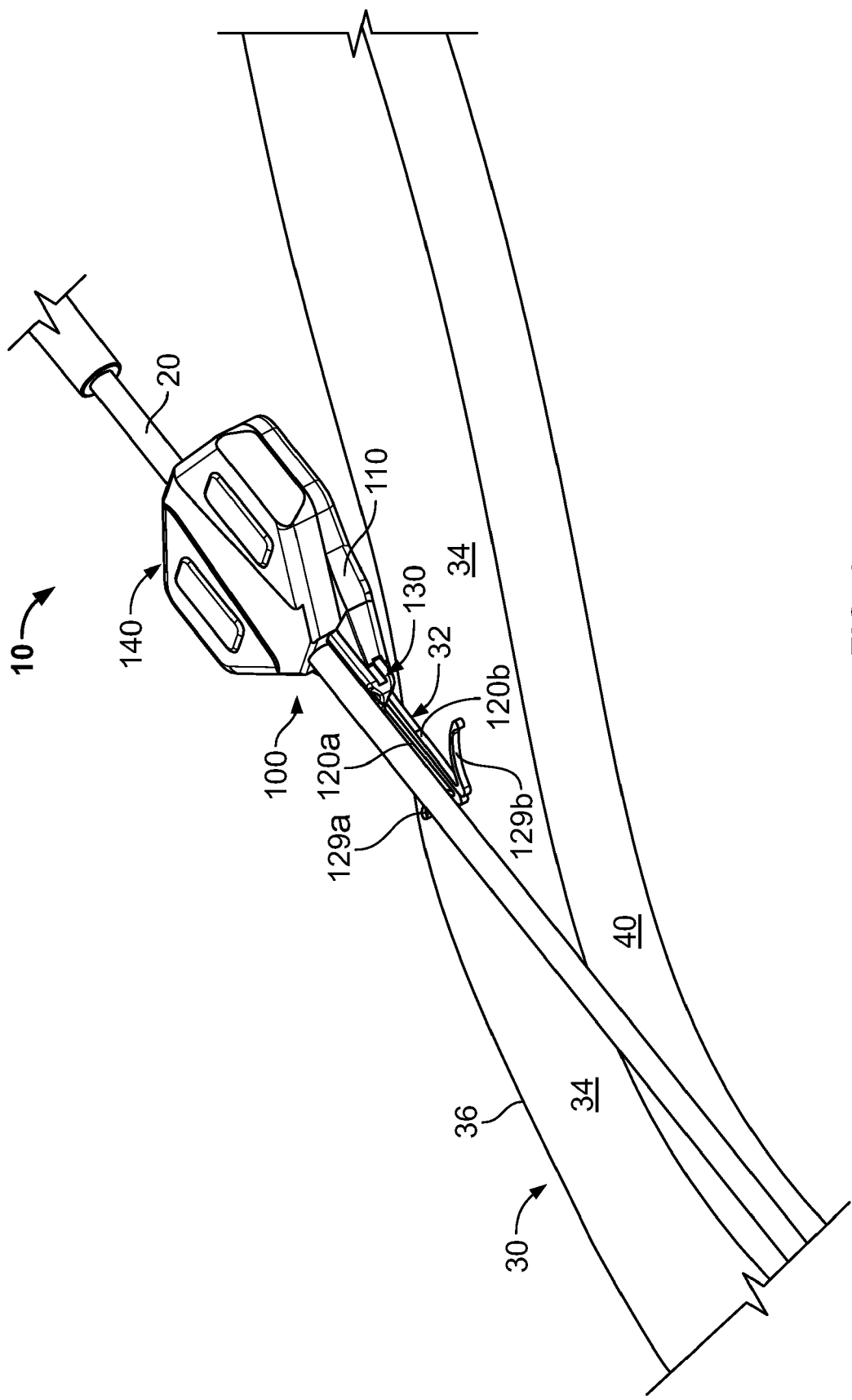
FIG. 1 is a perspective view of a system with a portion of an anchor device located in a subcutaneous region, in accordance with some embodiments.

Referring to FIG. 1, some embodiments of a medical device anchor system 10 include an anchor device 100 that releasably retains a medical instrument 20 (e.g., depicted as a catheter in this embodiment) in an operative position relative to a skin penetration point 32. The anchor device 100 may include a retainer body 110 that receives the medical instrument 20 and can releasably engage with an outer surface of the medical instrument 20. The medical instrument 20 extends from the retainer body 110 and through the penetration point 32 in the patient's skin 30 (e.g., through an incision or the like), while the retainer body 110 remains outside of the skin 30. As described in more detail below, the anchor device 100 can secure the catheter 20 in the operative position relative to the penetration point 32 without necessarily requiring sutures or adhesive tapes bonded to the skin. In this embodiment, the anchor device 100 can include an actuator 130 that can be activated to shift one or more anchors 120a-b distally from the retainer body 110. As such, the anchors 120a-b can be directed to penetrate through the same skin opening as the medical instrument 20. The anchors 120a-b can include tines 129a-b that, after insertion, are deployed in a subcutaneous region 34 (e.g., a region under the skin 30 that can comprise a fatty tissue layer) so as to secure the position of the anchor device 100—and the medical instrument 20 retained therein—relative to the skin penetration point 32.

In some embodiments, the medical instrument 20 can include a catheter that can be inserted through the penetration point 32 of the skin 30 as part of a medical procedure. For example, in the embodiment depicted in FIG. 1, a central venous catheter 20 can be inserted into a percutaneous opening surgically formed in the skin (e.g., penetration point 32), to the underside of the skin 30, and into a vein 40 to provide vascular access for delivering medications or minimally invasive devices into a patient. As described in greater detail below, after placement of the catheter 20, the anchor device 100 (arranged in the open configuration as shown in FIG. 3) can be guided along the catheter 20 and toward the penetration point 32. When a mouth 113 (FIG. 2) of the retainer body 110 reaches the penetration point 32, the user can adjust the actuator 130 so as to extend the anchors 120a-b distally from the retainer body 110. As such, the tips 122a and 122b (FIG. 2) of the anchors 120a and 120b are urged into the skin 30 through the penetration point 32. When the anchors 120a-b are inserted through the penetration point 32, the tines 129a and 129b can pass through the penetration point with reduced trauma to the surrounding skin tissue. As the anchors 120a and 120b are collectively advanced through the penetration point 32, the tines 129a and 129b are moved beneath the dermal layers 36 (e.g., the dermis, the epidermis, etc.) of the skin 30. When the tines 129a and 129b reach the subcutaneous region 34, the tines 129a and 129b can deploy in the subcutaneous region 34. As shown in FIG. 1, the anchors 120a and 120b may be designed such that the tines 129a and 129b include a curvature that abuts against the underside of the dermal layers 36 in a manner that reduces the likelihood of the tines 129a and 129b puncturing through the underside of the dermal layers 36. When the tines 129a and 129b of the anchors 120a and 120b are deployed in the subcutaneous region 34, the anchor device 100 can be secured to the patient without the retainer body 110 penetrating though the skin 30 of the patient and without necessarily requiring sutures or adhesive tapes to bond the retainer body 110 to the skin 30.

Figure 2:
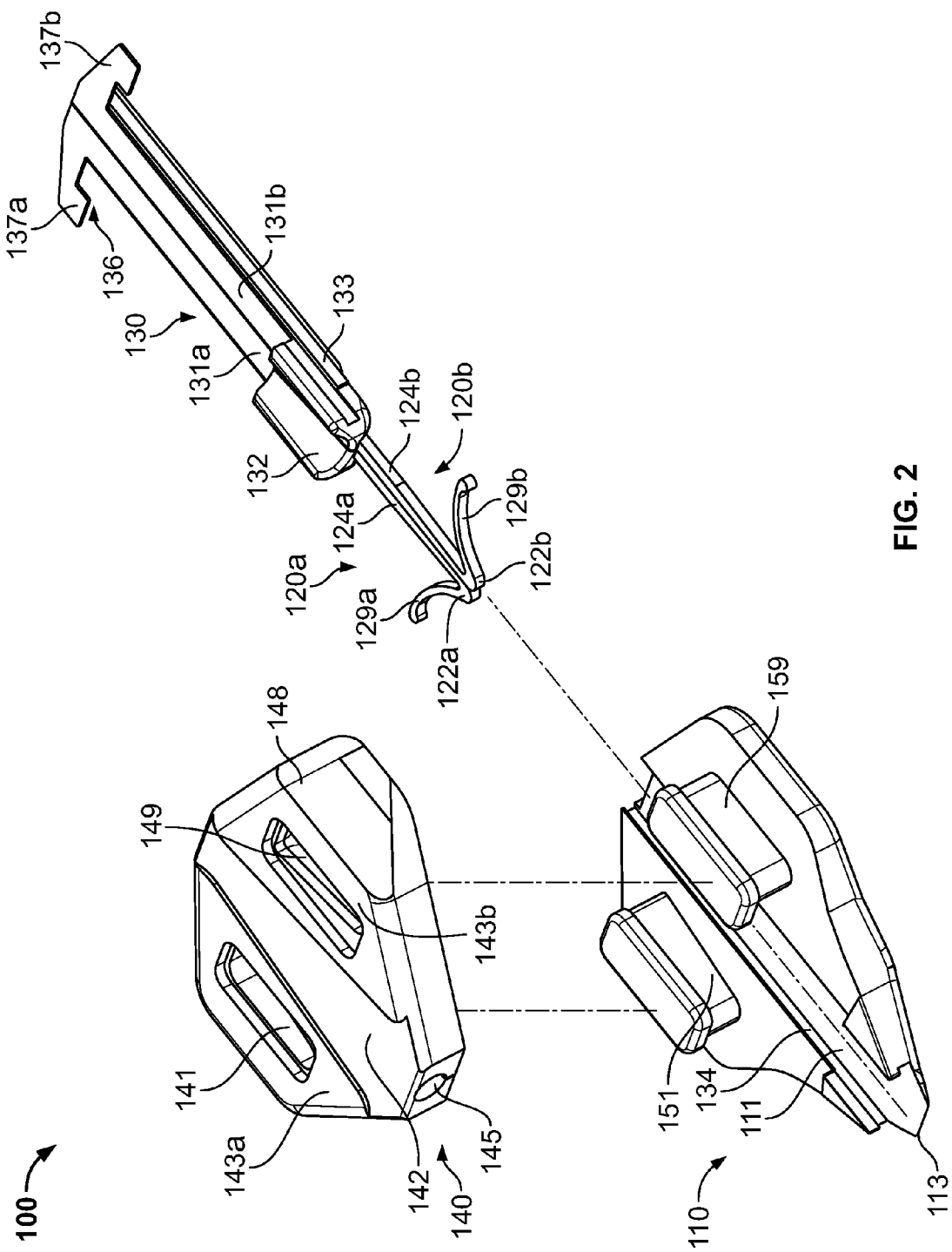
FIG. 2 is an exploded view of the anchor device of FIG. 1.
Figure 3:
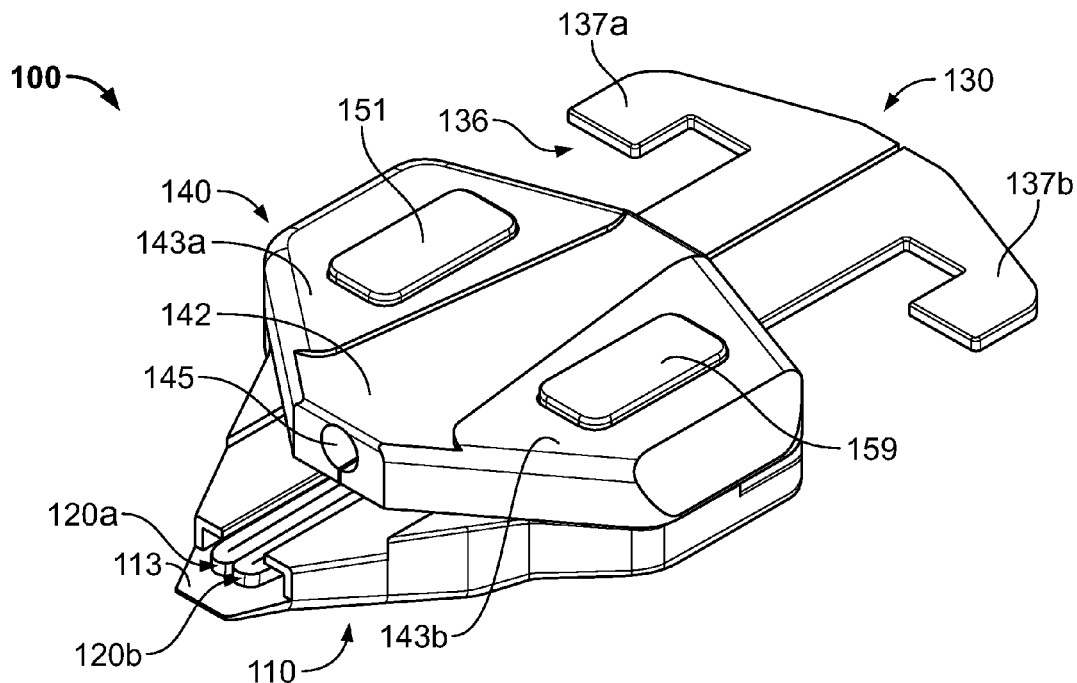
FIG. 3 is a perspective view of the anchor device of FIG. 1 in a non-deployed configuration.

Referring now to FIGS. 1 and 2, in some embodiments, the actuator 130 can be movably coupled to the retainer body 110 so as to shift the tines 129a-b from a non-deployed position to a deployed position. Actuator 130 includes anchors 120a-b that forwardly extend from respective first and second actuator body portions 131a and 131b. In some embodiments, the anchors 120a-b include over-molded portions (not shown in FIG. 1 or 2) that extend into respective actuator body portions 131a-b to give the anchors 120a-b rigidity and support.

In one embodiment, the actuator 130 mates with a channel 111 at least partially defined by the retainer body 110 such that the actuator 130 can slide longitudinally forward and rearward relative to the channel 111. The actuator 130 can include a tongue portion 133 on opposing sides of the actuator 130 that slidably couples the actuator 130 with a groove portion 134 on the retainer body 110. Such a mating configuration guides the sliding motion of the actuator 130 relative to the retainer body 110.

In some embodiments, the actuator 130 includes a stop member 136 (FIG. 2) that can limits the travel of the anchors 120a-b in the longitudinal direction. As shown in FIG. 2, the stop member 136 can include wings 137a-b that engage the retainer body 110 to prevent the actuator 130 from advancing further in the longitudinal direction relative to the retainer body 110 during deployment of the anchors 120a-b. In some embodiments, the stop member 136 positively locks into a fixed position when it engages the retainer body 110 so as to prevent the actuator 130 from prematurely "backing out" of the retainer body 110. In some embodiments, the stop member 136 is adjustable so as to permit the retainer body 110 to decouple from the anchors 120a-b (e.g., during removal of the catheter 20), as described in more detail below.

The actuator 130 can include two or more components (e.g., body portions 131a-b) that are releasably secured together by the retainer body 110. Such a configuration permits the anchors 120a-b to be coupled together during insertion into the skin penetration point 32, but then the anchors 120a-b can be readily separated from one another (after the retainer body 110 disengages the actuator 130) to facilitate individual removal from the skin. For example, when the tines 129a-b are being deployed through the skin penetration point 32, the actuator body portions 131a-b are coupled in a side-by-side abutting relationship such that the anchors 120a-b are retained substantially adjacent to each other. Thereafter, the actuator 130 can separate from the retainer body 110 (described below in connection with FIGS. 6G-H) so that the body portions 131a-b are movable relative to one another. As such, the actuator 130 can be separated into two components—the first body portion 131a (from which the first anchor 120a extends) and the second body portion 131b) (from which the second anchor 120b extends).

Still referring to FIGS. 1 and 2, the retainer body 110 can include an instrument retention member 140 used to secure the catheter 20 (or other medical instrument) relative to the skin penetration point 32. For example, after the catheter 20 is delivered into the targeted vein 40 (or other bodily lumen) and after the anchors 120a and 120b are deployed in the subcutaneous region 34, the retention member 140 can be applied to the catheter 20 to secure its position relative to the retainer body 110 (as described below).

In one embodiment, the retention member 140 can be releasably coupled to the catheter 20 through a frictional engagement (e.g., compression along an outer wall of the catheter 20), although other coupling mechanisms can be implemented. Because the retention member 140 may be coupled with the retainer body 110 (which is secured to the penetration point 32 by the deployed anchors 120a-b), the anchor device 100 can be used to temporarily secure the catheter 20 relative to the penetration point 32.

In this embodiment depicted in FIGS. 1 and 2, the retention member 140 may be removably attached to the retainer body 110 using one or more apertures 141 and 149 that mate with corresponding extensions 151 and 159. The retention member 140 may comprise a flexible material, such as silicone or another biocompatible polymer material. For example, at least a flexible wall portion 142 may comprise silicone or another biocompatible polymer material so that a second region 143b can flexibly adjust relative to a first region 143a. In such circumstances, the apertures 141 and 149 can be forced over the corresponding extensions 151 and 159, and thereafter (if desired) one aperture 149 can be lifted from the retainer body 110 while the another aperture 141 remains secured to the retainer body 110, as described below.

The retention portion 140 can secure the catheter 20 relative to the skin penetration point 32 throughout the medical procedure in which the catheter 20 is employed. For example, after the catheter 20 is delivered into the targeted vein 40 (or other bodily lumen) and after the anchors 129a-b are deployed in the subcutaneous region (proximate to the skin penetration point), the retention member 140 can be adjusted so that the catheter 20 is frictionally engaged inside a channel 145. In particular, the retention member 140 can be transitioned from an open configuration (refer to FIG. 6B) to a closed configuration (refer to FIG. 6C) to thereby secure the catheter 20 within the channel 145 of the retention member 140. The channel 145 may be at least partially defined by a wall comprising silicone or another flexible polymer that compresses against, and applies a holding force to, the outer surface of the catheter 20 (without compromising the operation of the internal catheter lumen(s)). As such, in some embodiments, the anchor device 100 can be secured to catheter 20 without the use of adhesives. It should be understood from the description herein that, in alternative embodiments, the anchor device 100 may include an adhesive pad to supplement the holding forces applied by the retention member 140.

In use, the anchor device 10 can include features that facilitate separation from the catheter 20 and removal from the skin in a manner that reduces the likelihood of trauma to the skin surrounding the penetration point. For example, the retention member 140 can include a tab 148 that can be readily grasped by a user to lift the second region 143b from the retainer body 110, thereby opening the channel 145 for removal of the catheter 20. After the retention member 140 is shifted to the open configuration (refer to FIG. 6D), the catheter 20 can be separated from the channel 145 and removed from the anchor device 100 (e.g., to withdraw the catheter 20 from the patient while the anchor device 100 remains secured to the skin penetration point 32). Moreover, the anchor device 100 can include separable portions that can be disassembled prior to removal of the anchors 120a-b from the subcutaneous region. For example, in this embodiment, the anchor device 100 comprises an assembly of two pieces (refer to FIG. 6I) that can separate from one another to facilitate removal of one anchor 120a independent of the other tine 120b. Such a configuration permits the anchors 120a-b to be maneuvered in a manner that reduces the likelihood of causing damage to the skin during removal.

Figure 4:
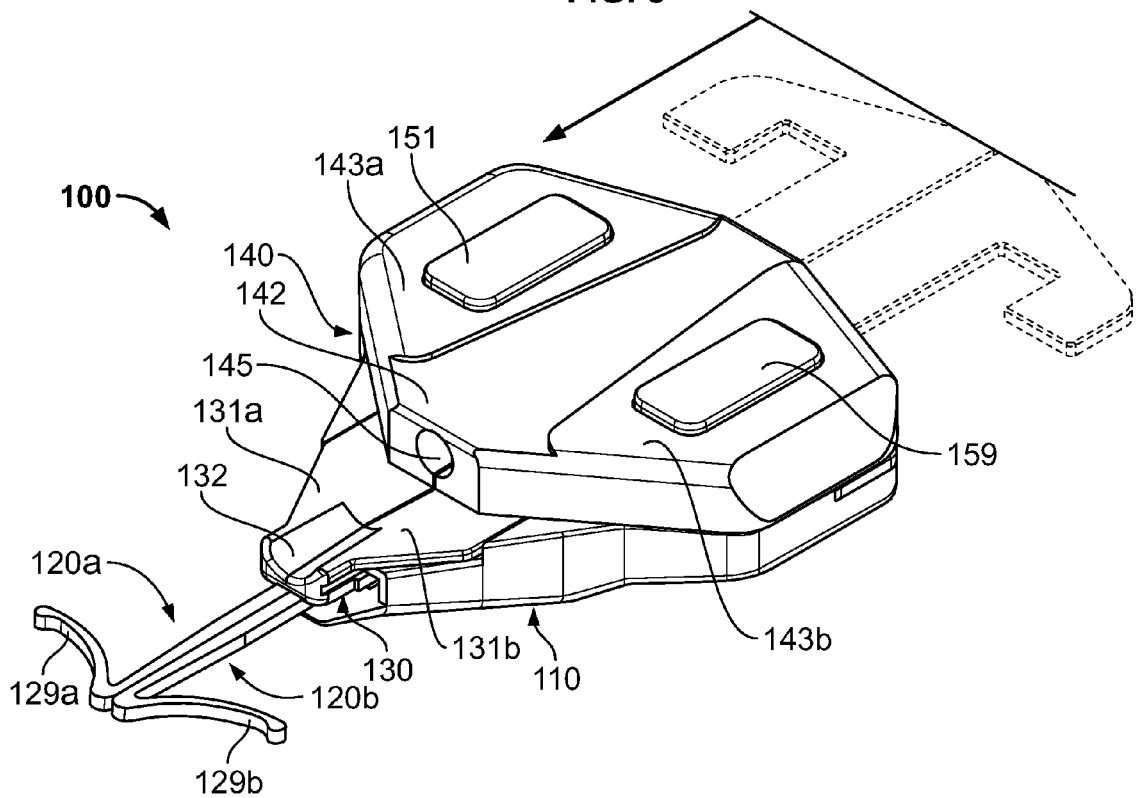
FIG. 4 is a perspective view of the anchor device of FIG. 1 in a deployed configuration.

Referring now to FIGS. 3-4, some embodiments of the anchor device 100 can be actuated so as to shift the anchors 120a-b from a non-deployed configuration to a deployed configuration. When the anchors 120a-b are arranged in the non-deployed configuration (FIG. 3), the entire anchor device 100 may reside outside the patient's body. As the mouth 113 of the anchor device 100 is delivered to the skin penetration point 32, the actuator 130 can adjust within the retainer body 110 so as to direct the anchors 120a-b through the skin penetration point 32 and into the deployed configuration (FIG. 4). The anchors 120a-b can include features that facilitate advancement into the subcutaneous region in a manner that reduces the likelihood of damage to surrounding tissue. For example, in some embodiments, the anchors 120a-b may comprise a material that exhibits superelasticity when used in a patient's body. As such, when the anchor tines 129a-b of anchors 120a-b are inserted through the skin penetration point 32, the tines 129a-b can superelastically flex from an expanded position to a contracted position (e.g., in which the tines are pressed against the sides of the anchor bodies 124a-b). While flexed toward the anchor bodies 124a-b, the tines 129a-b can readily penetrate through the skin penetration point 32 (which may be generally smaller in width than the width occupied by the tines 129a-b in a fully expanded state). Such anchor insertion techniques can reduce the damage to the patient's skin 30 during deployment of the anchors 120a-b.

In the embodiments in which the anchors 120a-b can superelastically flex, at least portions of the anchors 120a-b (including the tines 129a-b) may be formed from a length of nitinol wire or from a sheet of nitinol material, which has been processed to exhibit superelasticity below or at about a normal human body temperature, such as below or at about 37 degrees C. The nitinol material may comprise, for example, Nickel Titanium (NiTi), Niobium Titanium (NbTi), and the like. Alternatively, the anchors 120a-b may comprise a metal material such as stainless steel (e.g., 304 stainless, 316 stainless, custom 465 stainless, and the like), spring steel, titanium, MP35N, and other cobalt alloys, or the like. In another alternative, the anchors 320a and 320b may be formed from a resilient polymer material. In these embodiments, the anchors 120a-b can be formed from a material or materials that allow the tines 129a-b to be flexed to a contracted position (e.g., as in FIG. 3) and can resiliently return to an expanded position (e.g., as in FIG. 4). To further decrease the insertion profile of the anchors 320a-b as they are inserted into the skin 30, the anchor bodies 324a and 324b can include recesses, such as the recess 326a and the corresponding recess (not shown) in the anchor body 324b into which at least a portion of the tines 322a-b can inwardly flex. As such, the recesses in the anchor bodies 324a-b can at least partially accommodate the tines 322a-b when they are flexed into the contracted position, thereby further reducing the insertion profile of the anchors 320a-b.

As shown in FIG. 3, the anchors 120a-b are arranged in a non-deployed configuration and contained within the actuator channel 111 of the retainer body 110. The tines 129a-b of the anchors 120a-b may be retained in a stressed position by the walls of the channel 111, and the tines 129a-b may be biased to outwardly flex upon advancing from the mouth 113 of the retainer body 110. In the configuration shown in FIG. 3, a rearward portion of the actuator 130 may extend from the proximal end of the retainer body 110 so that a user can apply an actuation force to the actuator 130. As previously described, the actuation force can be applied to the actuator 130 so that the actuator 130 is advanced in the longitudinal direction within the channel 111 of the retainer body.

As shown in FIG. 4, the actuator 130 is adjusted relative to the retainer body 110 so that the anchors 120a-b can exit the mouth 113 and shift toward the deployed configuration. In this embodiment, the rearward portion of the actuator 130 has been advanced by the actuation force so that the stop member 136 engages a complementary cavity of the retainer body 110. As such, the stop member 136 can limit the distal motion of the anchors 120a-b during deployment through the skin penetration point 32. When the anchors 120a-b are shifted to the deployed configuration, the anchors 120a-b extend distally from the retainer body 110. In these circumstances, the anchors 120a-b can be deployed in the subcutaneous region 34 (FIG. 1) while the remaining portions of the anchor device 100 reside outside the skin. Thus, the anchor device 100 may engage the medical instrument (e.g., catheter 20) outside the skin while the anchors 120a-b extend distally through the same skin penetration point 32 occupied by that medical instrument (e.g., catheter 20).

Figure 5:
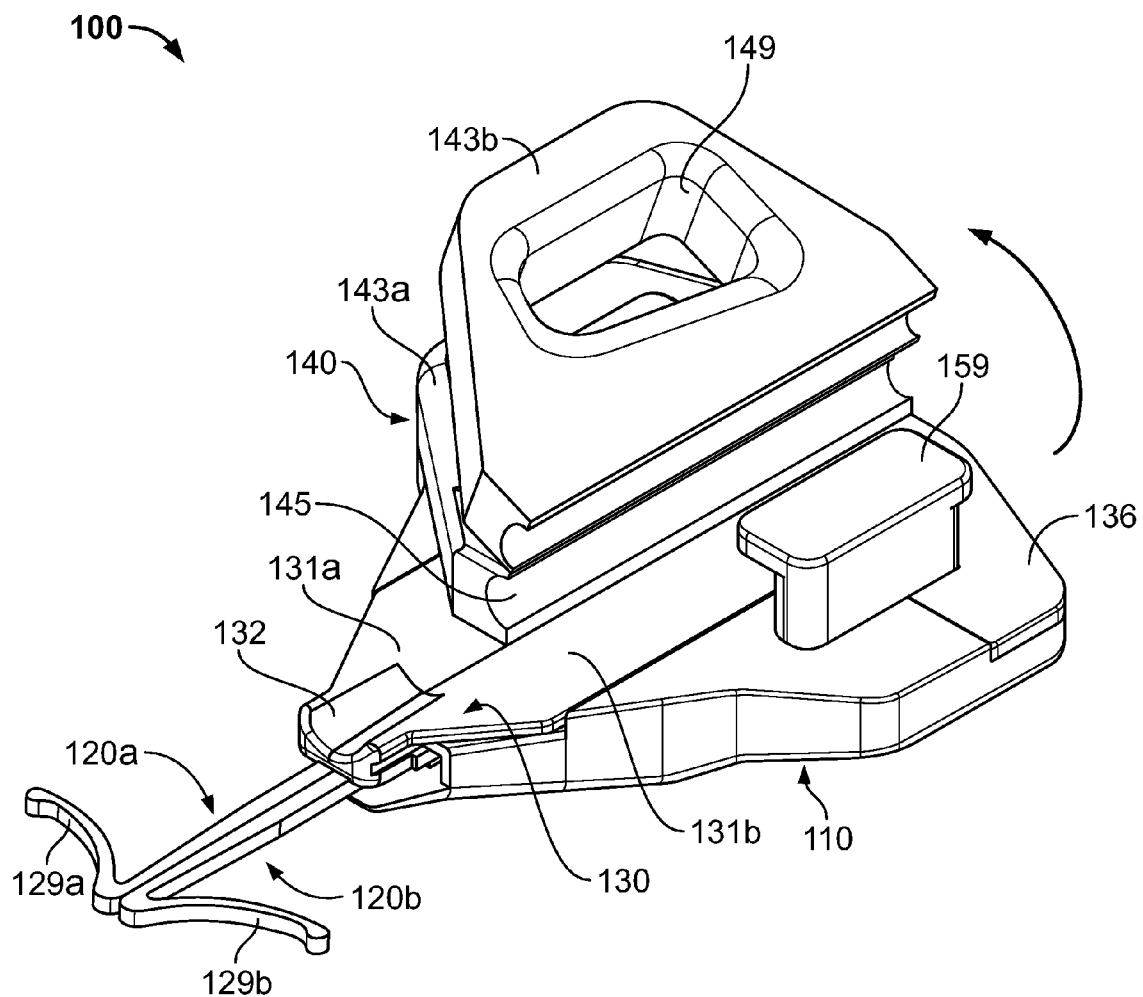
FIG. 5 is a perspective view of the anchor device of FIG. 1 in an opened position.

Referring now to FIGS. 4-5, the retention member 140 of the anchor device 100 can be shifted between a closed position (FIG. 4) and an open position (FIG. 5) so as to releasably engage the medical instrument (e.g., the catheter 20 in this particular embodiment). As previously described, the retention member 140 may, in certain embodiments, include regions 143a-b that can adjust relative to one another so as to reveal the channel 145 therebetween (e.g., to insert a portion of the medical instrument). The regions can be movable joined at an interface that includes, for example, one or more folds, creases, micro-hinges, perforations, or the like. The retainer body 110 can includes locking posts 151 and 159 that serve to releasably secure the retention member 140 in the closed position. For example, the retention member 140 may be removably attached to the retainer body 110 using the apertures 141 and 149 that mate with the corresponding posts 151 and 159. The retention member 140 may comprise silicone or another flexible material so that the second region 143b can flexibly adjust relative to the first region 143a. Accordingly, the apertures 141 and 149 can be forced over the corresponding posts 151 and 159, and thereafter the user may lift the second region 143b from the retainer body 110 while the first region 143a remains secured to the retainer body 110 (refer to FIG. 5). This adjustment of the retention member 140 provides access to the channel 145 so that the catheter 20 or other medical instrument can be arranged therein. When the retention member 140 is returned to the closed position (refer to FIG. 4), the wall of the channel 145 can compresses against, and apply a frictional engagement to, the outer surface of the catheter 20.

Referring now to FIGS. 6A-6I, some embodiments of the anchor device 100 can be implemented to secure a medical instrument at a selected location on a patient's body. For example, the anchor device 100 can be used in certain processes to secure the catheter 20 in a selected position relative to the skin penetration point 32 that is occupied by the catheter 20. Moreover, the anchor device 100 may properly secure the catheter 20 in this operative position without necessarily requiring sutures or adhesive tapes bonded to the skin.

Figure 6A:
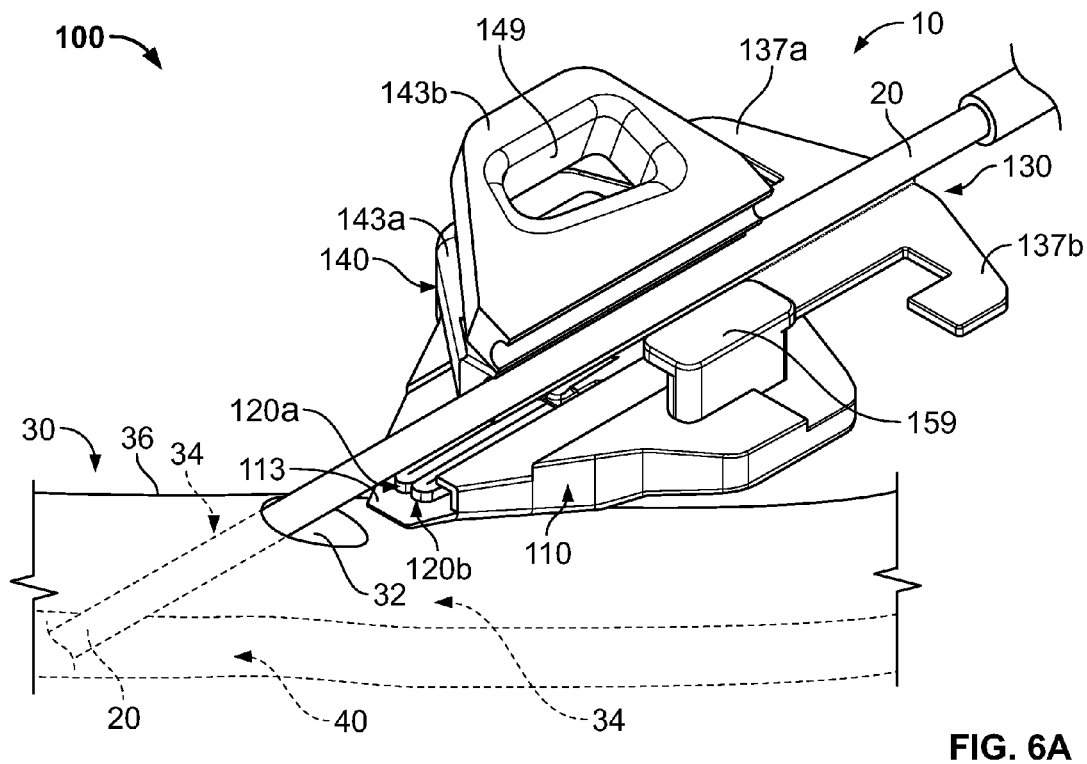
FIGS. 6A-I are perspective views of an exemplary implementation of the anchor device of FIG. 1.

As shown in FIG. 6A, a medical instrument (in this particular example, a catheter 20) has been delivered through a patient's skin 30, through the subcutaneous layer 34, and into a targeted vein 40. After the catheter 20 is advanced through the skin, the anchor device 100 can be directed along the catheter 20 and toward the skin penetration point 32 that is occupied by the catheter. As previously described, the skin penetration point 32 can be formed, for example, by an incision in the skin 30. In this embodiment, the anchor device 100 is advanced along the outer surface of the catheter 20 while the retention member 140 is in the open position. As such, a guide channel 132 (FIG. 2) defined by the actuator 130 can be guided by the outer surface of the catheter 20 while the anchor device 100 is advanced toward the skin penetration point 32. When the mouth 113 (FIG. 2) of the anchor device 100 is arranged proximate to the skin penetration point 32, the user can prepare to shift the anchors 120a-b away from the non-deployed configuration.

Figure 6B:
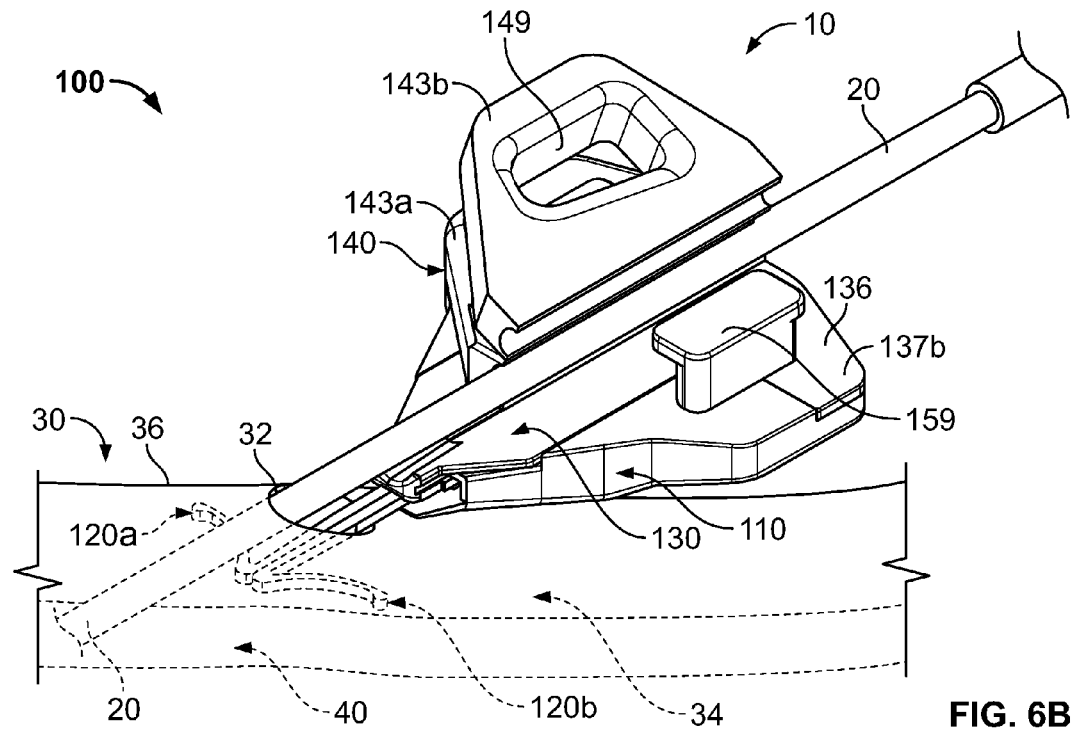

Referring to FIG. 6B, the anchor device 100 can be secured to the skin penetration point 32 by deploying anchors 120a-b through the skin penetration point 32 and into the subcutaneous layer 34. As previously described, the user can adjust the actuator 130 so as to advance the anchors 120a-b out of the mouth 113 and through the skin penetration point 32. For example, the user can deploy the anchors 120a-b by applying a force to the actuator 130 that causes the actuator 130 adjust in the distal direction until the stop member 136 engages the mating cavity of the retainer body 110, thus limiting further longitudinal movement of the anchors 120a-b. In some embodiments, the stop member 136 of the actuator 130 positively engages with the retainer body 110 such that the actuator 130 locks in the deployed position and thereby reduces the likelihood of the anchor device 100 prematurely releasing from the skin 30. In this embodiment, the catheter 20 is depicted as being positioned in the channel 145 of the retention member 140 (in the open position) before the anchors 120a-b are deployed into the skin penetration point 32. It should be understood from the description herein that, in other embodiments, the catheter 20 may be fit into the channel 145 after the anchors 120a-b are deployed into the subcutaneous layer 34.

Figure 6C:
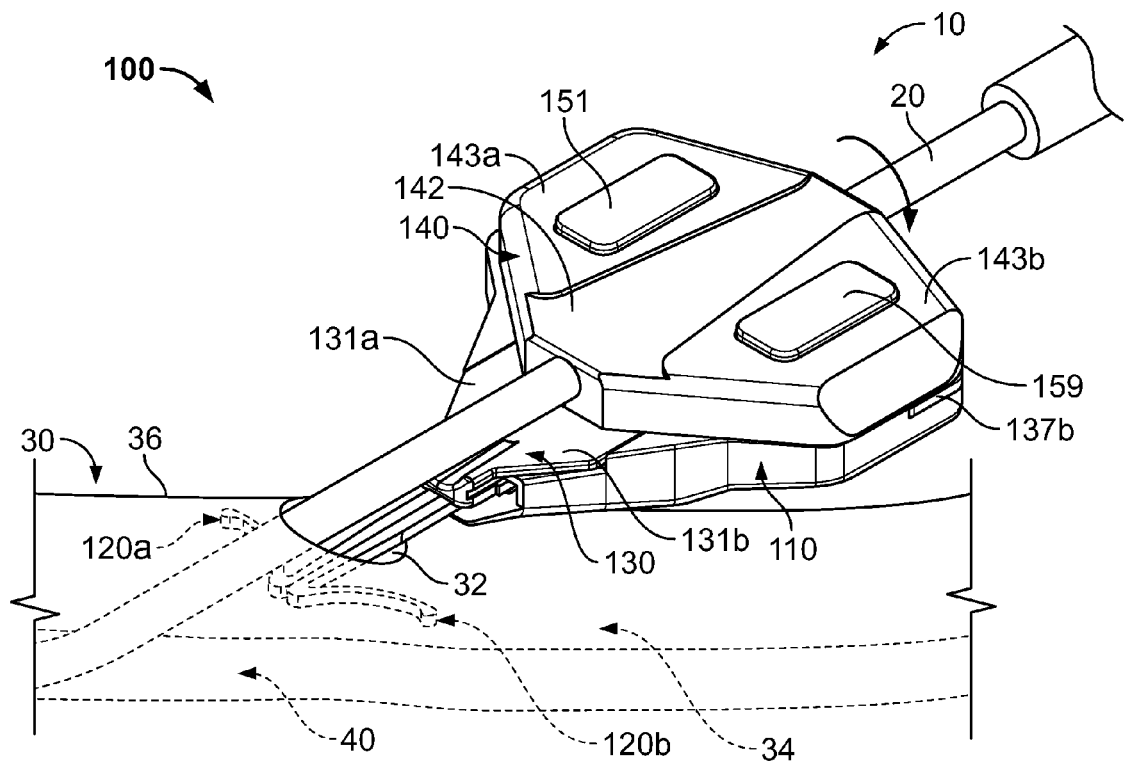

As shown in FIG. 6C, the retention member 140 can be adjusted to the closed position so as to retain the catheter 20 in the selected position. Thus, after the catheter 20 is delivered into the targeted vein 40 (or other bodily lumen) and after the anchors 120a-b are deployed in the subcutaneous region 34, the retention member 140 can lockingly engage the catheter 20 to secure its position relative to the retainer body 110. As previously described, the retention member 140 can be releasably coupled to the catheter 20 through a frictional engagement (e.g., compression along an outer wall of the catheter 20), which provides a temporarily holding force on the catheter 20 relative to the penetration point 32. In this embodiment, the retention portion 140 can secure the catheter 20 relative to the skin penetration point 32 throughout the medical procedure in which in the catheter 20 in employed. The configuration illustrated in FIG. 6C shows the anchor device 100 as it may be used to secure a patient's catheter 20 over a period of time, for example, for hours, one to seven days, or longer. As previously described, the retention member 140 can be transitioned from the open position (refer to FIG. 6B) to the closed position (refer to FIG. 6C) by securing the first and second regions 143a-b to the corresponding locking posts 151 and 159 (e.g., so that the channel 145 substantially surrounds the catheter 20).

Referring now to FIGS. 6D-6I, the catheter 20 may be withdrawn from the patient (e.g., after the procedure) while the anchors 120*a-b* remain in the subcutaneous region 34. In some embodiments, the anchors 120*a-b* may be coupled together (as part of the fully assembled anchor device 100) during insertion into the skin penetration point 32 (refer to FIG. 6B), but thereafter the anchors 120*a-b* can be readily separated from one another to facilitate removal from the skin (refer to FIG. 6I). Accordingly, the anchors 120*a-b* and associated tines 129*a-b* can collectively penetrate into the subcutaneous layer 34 as part of the assembled device 100, and may be separately and individually withdrawn from the penetration point 32 during the removal process.

Figure 6D:
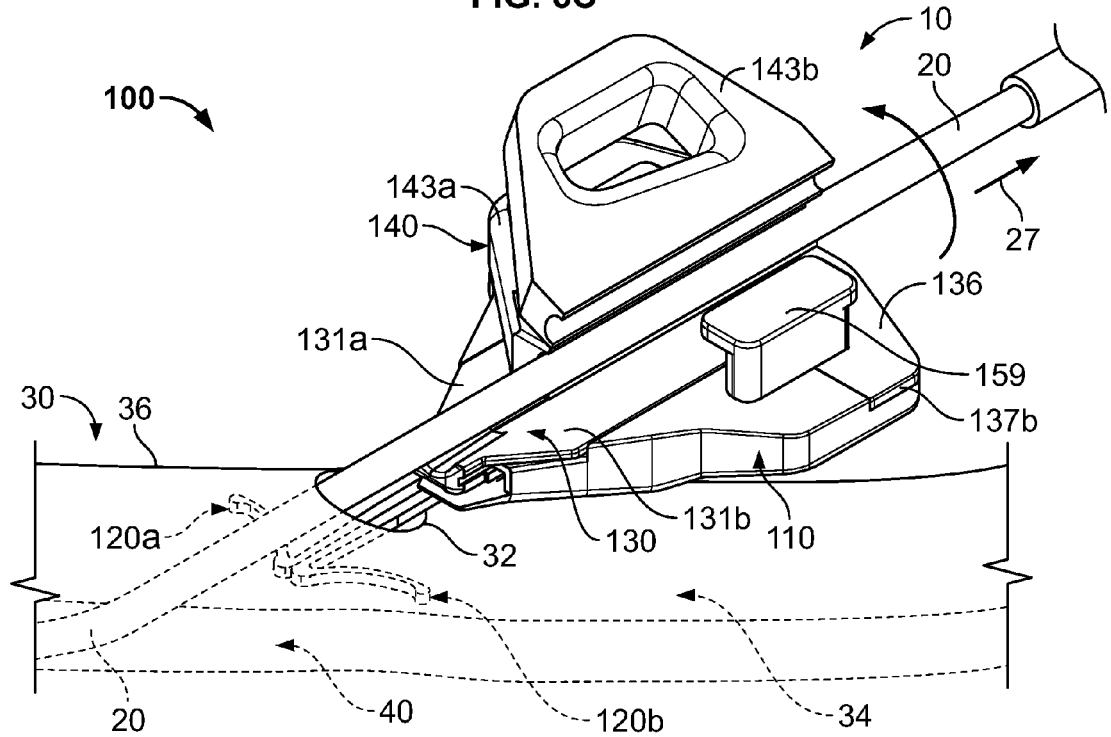

In the embodiment depicted in FIG. 6D, when the catheter 20 is to be removed from the skin 30, the catheter 20 may be released from the retention member 340 by lifting at least one of the regions 143*a-b* from the locking posts 151 and 159 (illustrated by the curved arrow in FIG. 6D). This adjustment of the second region 143*b* relative to the locking post 159 effectively releases the grip on the catheter 20 and allows the catheter 20 to be withdrawn the catheter 20 from the patient's skin 30. In some implementations, the guide channel 132 (FIG. 2), the opened channel 145, or both may be used as a guide in removing the catheter 20 to thereby reduce trauma to surrounding tissue.

Figure 6E:
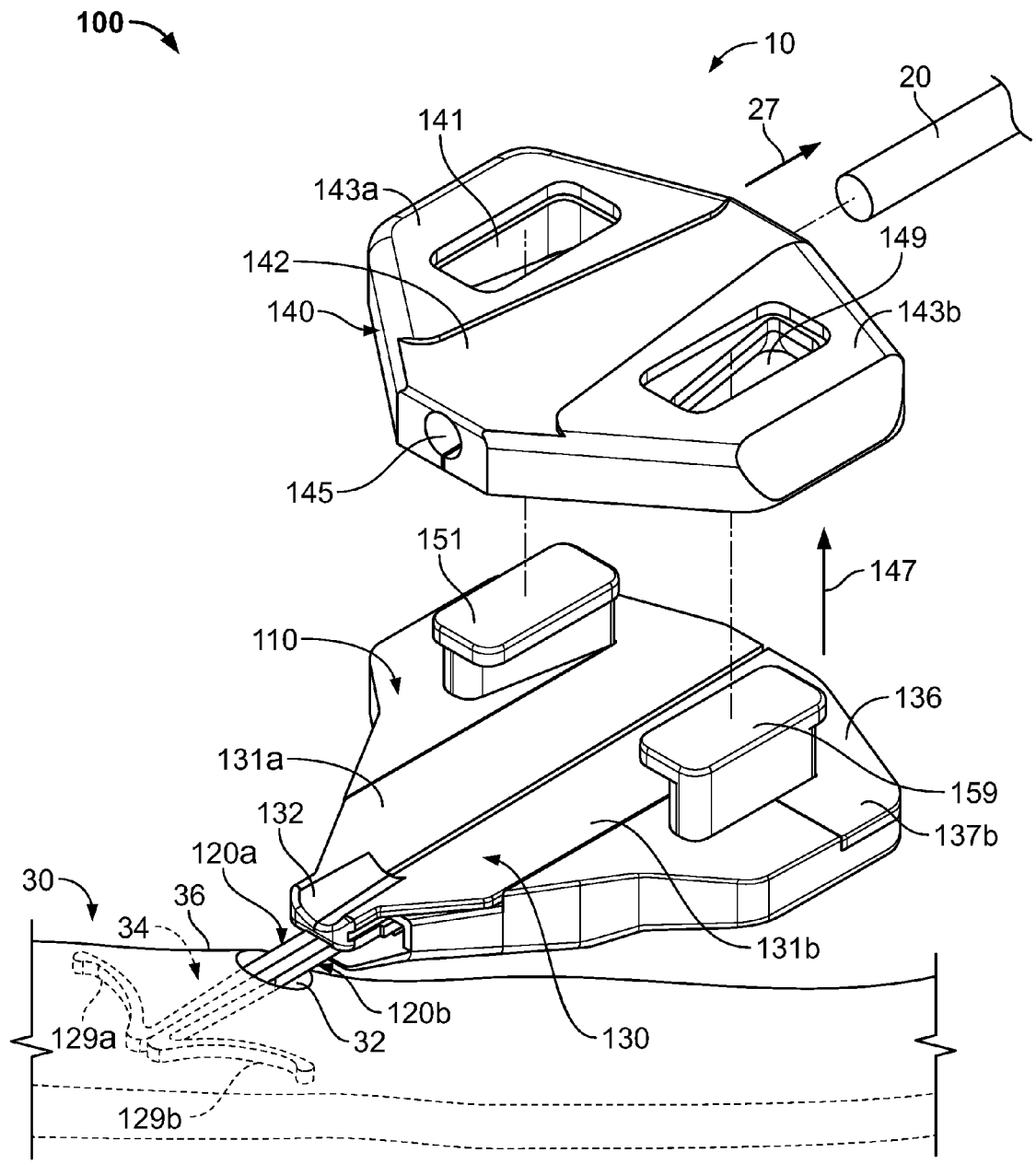

As shown in FIG. 6E, after the catheter withdrawal force 27 is applied to retract the catheter 20 from the skin 30, the anchor device 100 can be removed. In this embodiment, the anchor device 100 can be removed from the patient through a disassembly procedure that allows the anchors 120*a-b* to decouple from the retainer body 110. After the anchors 120*a-b* are free from the retainer body 110, they can be individually maneuvered in such a way as to reduce the likelihood of damage to the skin tissue during removal. The retention member 340 can be removed from the retainer body 110, for example, by applying a lifting force 147 to regions 143*a-b* to overcome the engagement between the apertures 141 and 149 and the locking posts 151 and 159, as illustrated in FIG. 6E. At this stage, the retainer body 110 and the retention member 140 are two distinctly separate pieces, and the retention member 140 can be discarded.

Figure 6F:
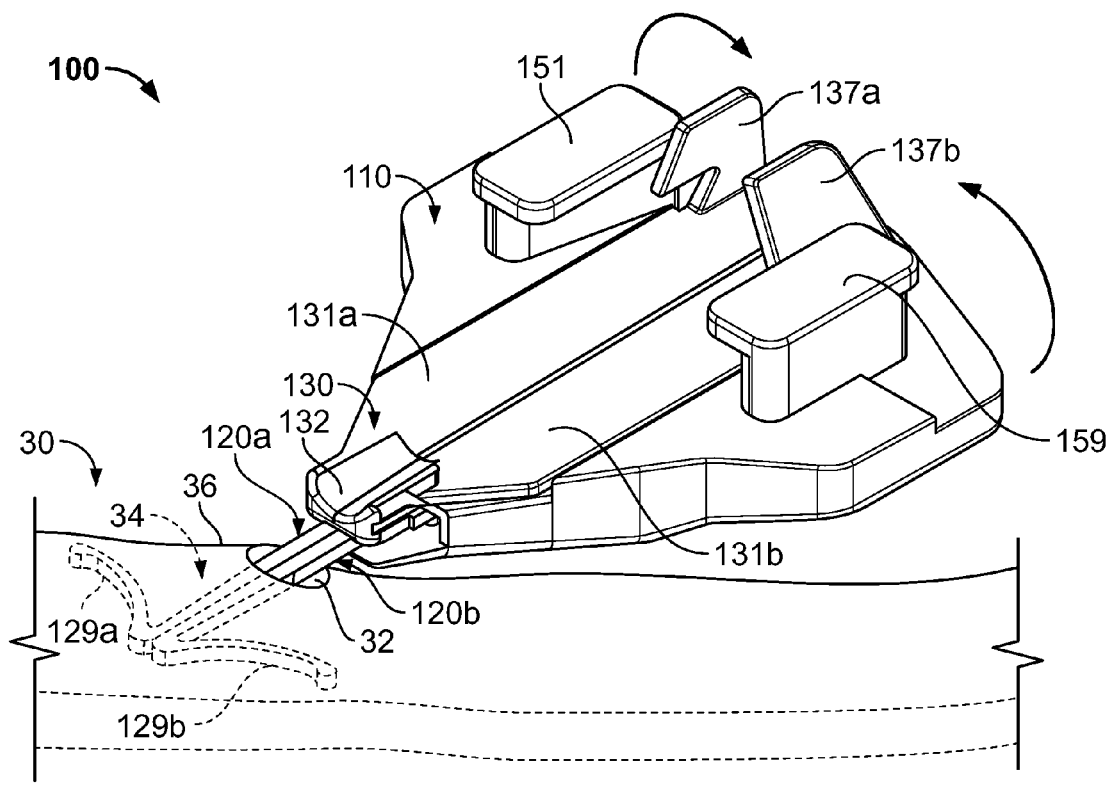
Figure 6G:
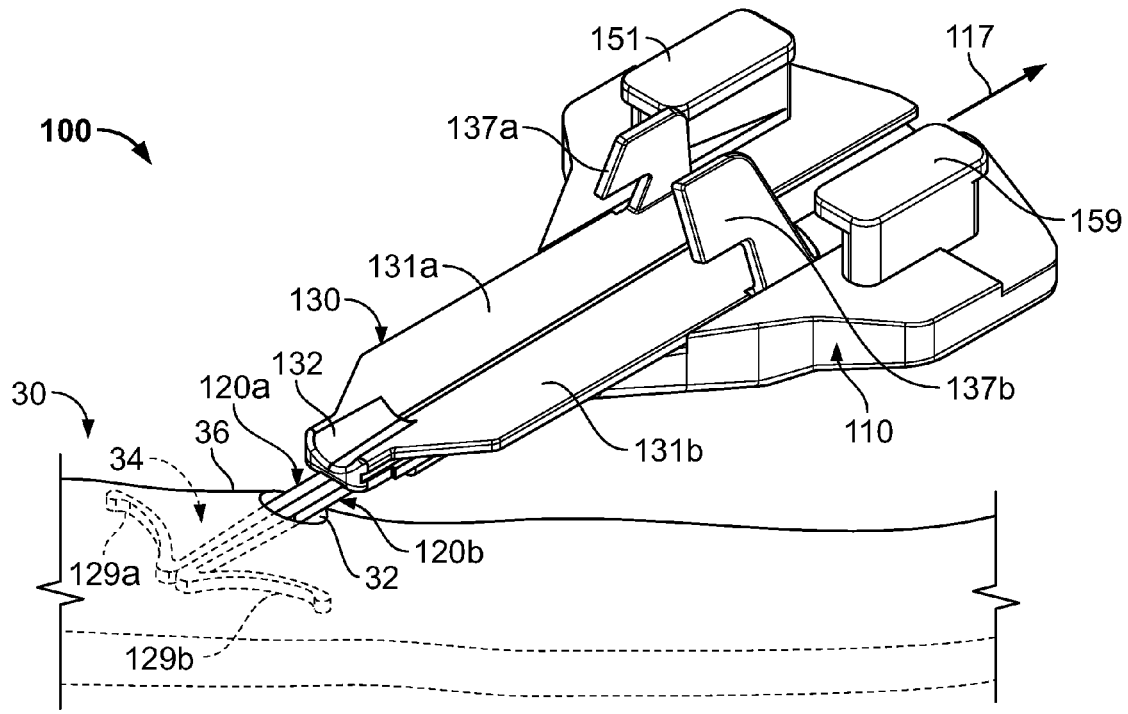
Figure 6H:
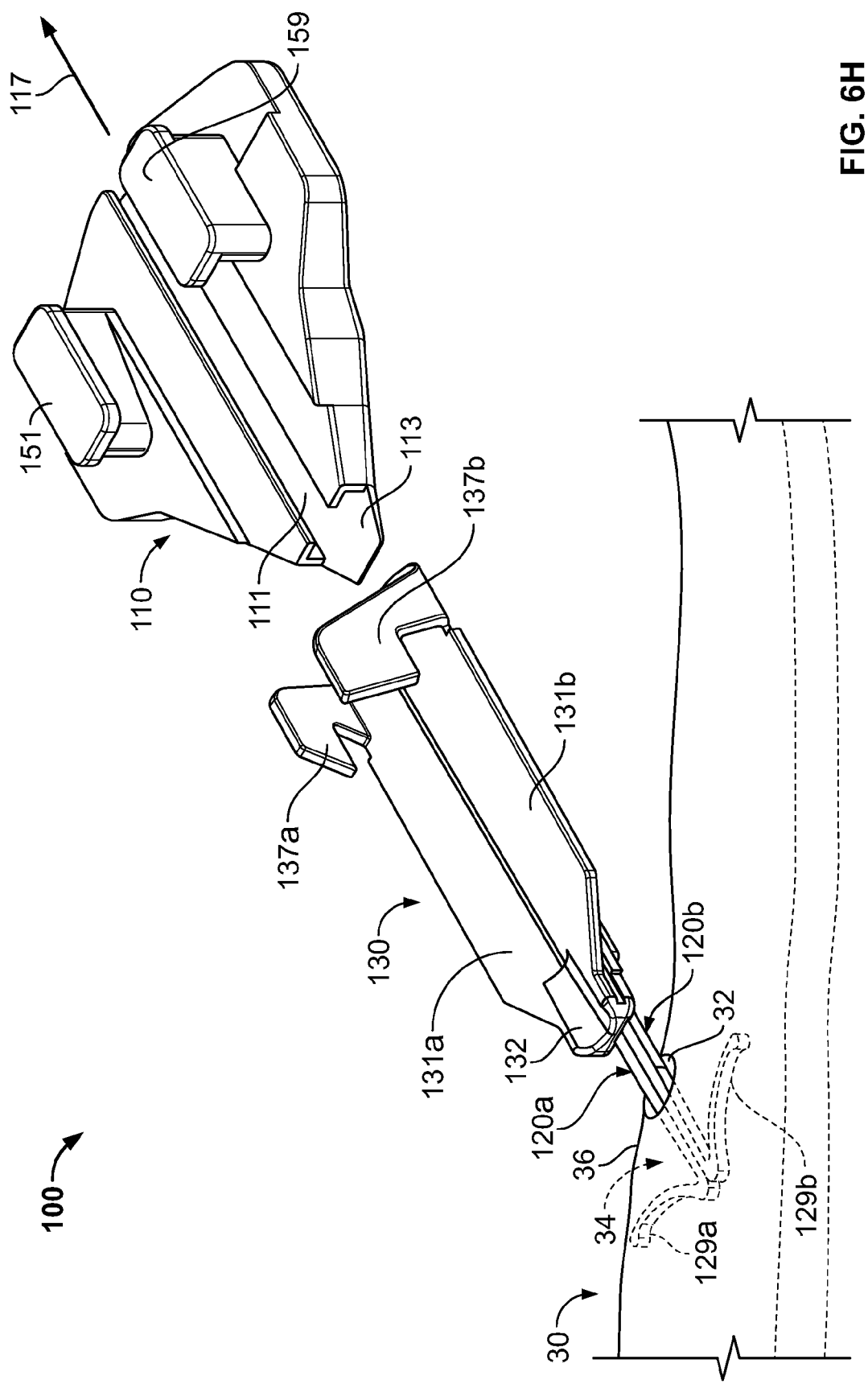

As shown in FIGS. 6F-H, the retainer body 110 can be decoupled from the anchors 120*a-b* while the anchors 120*a-b* remain engaged with the skin 30. In one embodiment, the stop member 136 of the actuator 130 can be adjusted to permit the release of the retainer body 110. For example, as shown in FIG. 6F, the actuator wings 137*a-b* can be adjusted to disengage the retainer body 110 so that the actuator 130 can slide through the channel 111. As shown in FIG. 6G, the retainer body 110 can be moved away from the skin penetration point 32 upon application of a removal force 117 on the retainer body 110. The removal force 117 may cause the retainer body 110 to slide longitudinally away from the anchors 120*a-b* until the retainer body 110 decouples from the actuator 130 and the anchors 120*a-b* (refer to FIG. 6H).

Figure 6I:
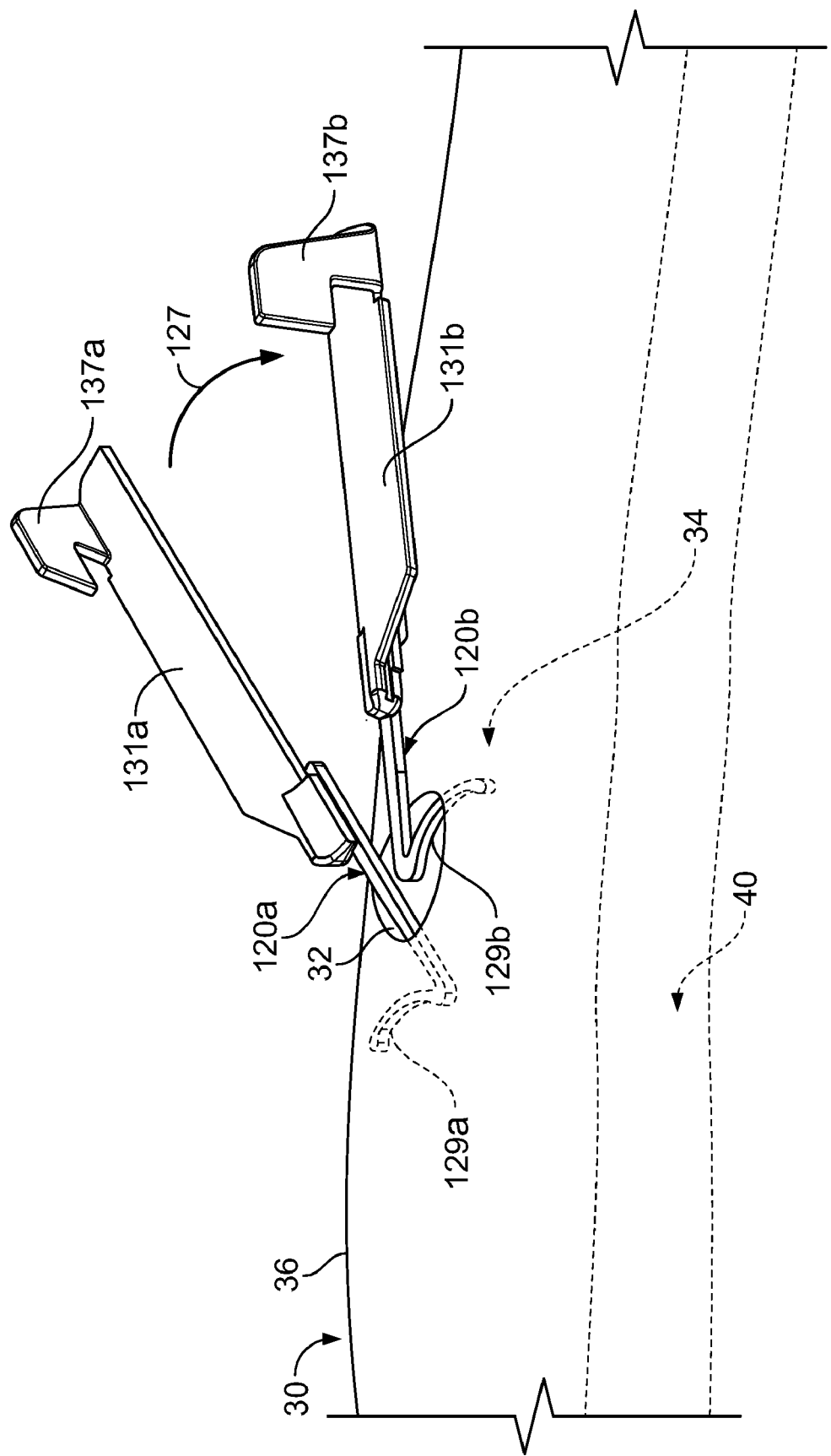

Referring now to FIG. 6I, the anchors 120*a-b* can be removed from the skin penetration point 32 in a manner that reduces the likelihood of damage to the surround skin tissue. As previously described, the anchors 120*a-b* may be separated and individually maneuvered so that one anchor 120*b* can be removed independent of the other anchor 120*a*. In this embodiment, the anchors 120*a-b* may be separated from one another after the retainer body 110 is removed and the body portions 131*a-b* can be separately manipulated by a user. The anchors 120*a-b* can be separated from each other by, for example, applying a separation force 127 to the second anchor 120*b*, which urges the second anchors 120*b* apart from the first anchor 120*a*. Thereafter, the anchors 120*b* can be separately and individually removed from the skin penetration point 32 by shifting the anchor 120*b* in a direction that favors release of the tine 129*b* from the subcutaneous layer 34. Similar movements can be repeated for the remaining anchor 120*a* so to completely remove the anchors 120*a-b* in a manner that reduces the likelihood of damage to the surround skin tissue.

It should be understood that, in some embodiments, the anchor device is not limited to the previously described configurations. For example, in particular embodiments, the deployment of an anchor system can be aided through the use of a delivery device (refer to FIGS. 10A-B). Also, the anchors can be released from the retainer body (e.g., to facilitate removal of the anchors) using other implementations (refer, for example, to FIG. 9).

Figure 7:
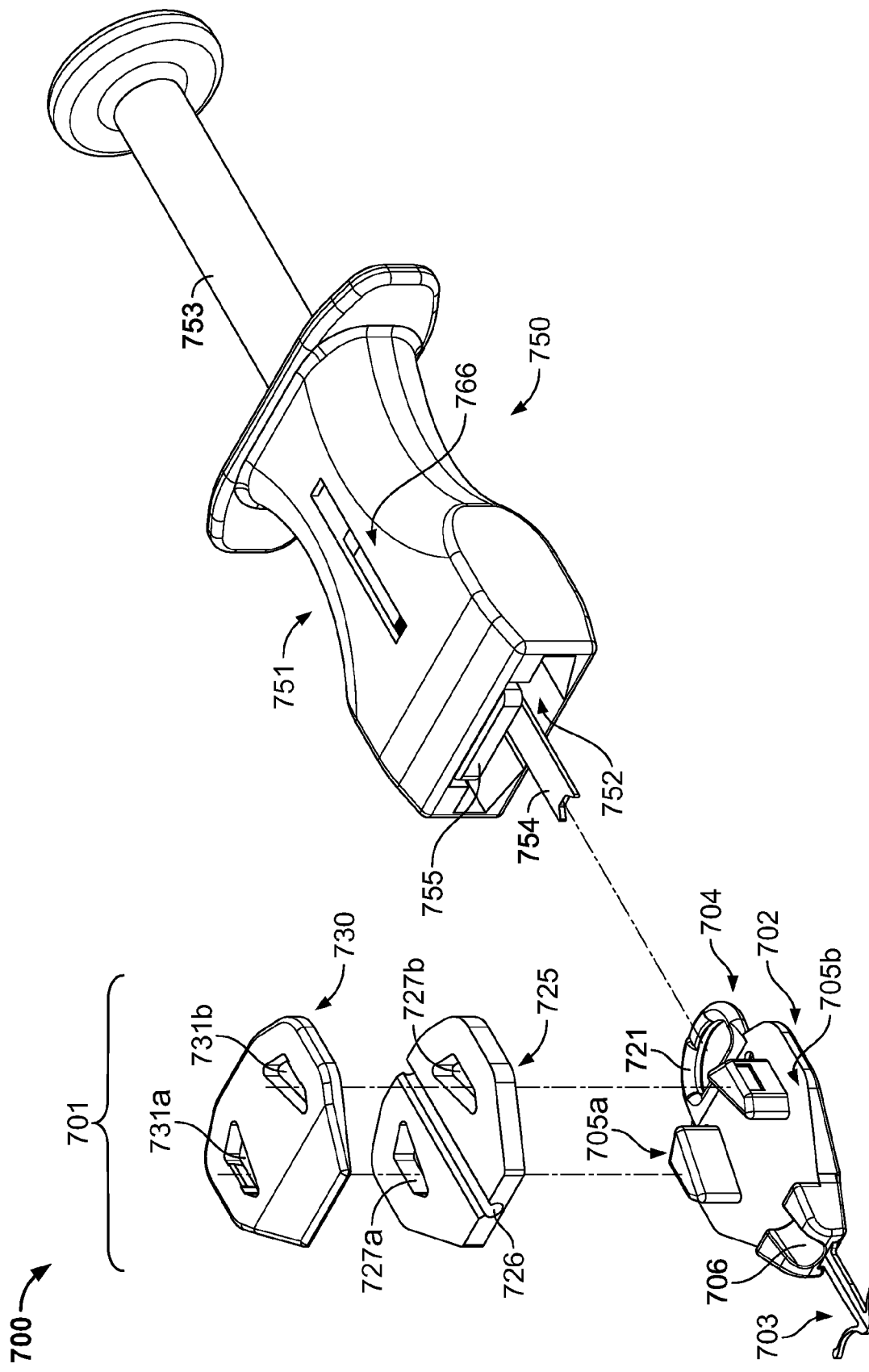
FIG. 7 is an exploded view of an anchor device, in accordance with further embodiments.
Figure 8:
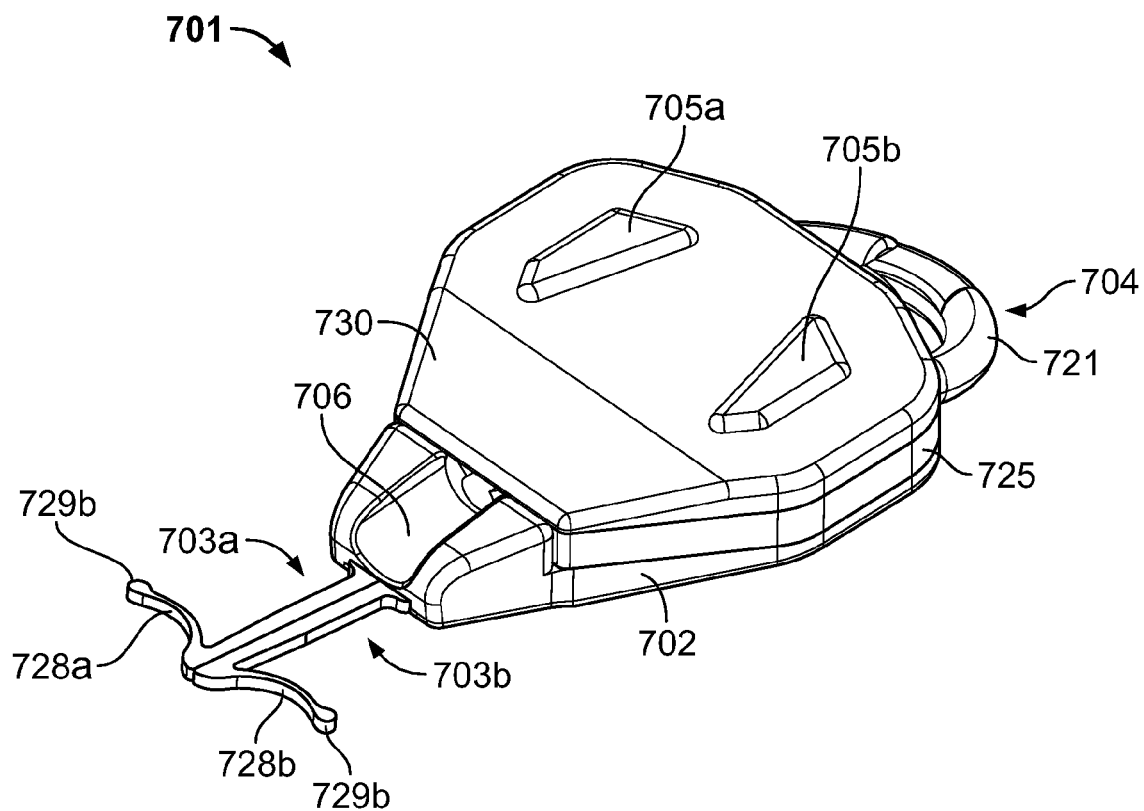
FIG. 8 is a perspective view of the anchor device of FIG. 7.
Figure 9:
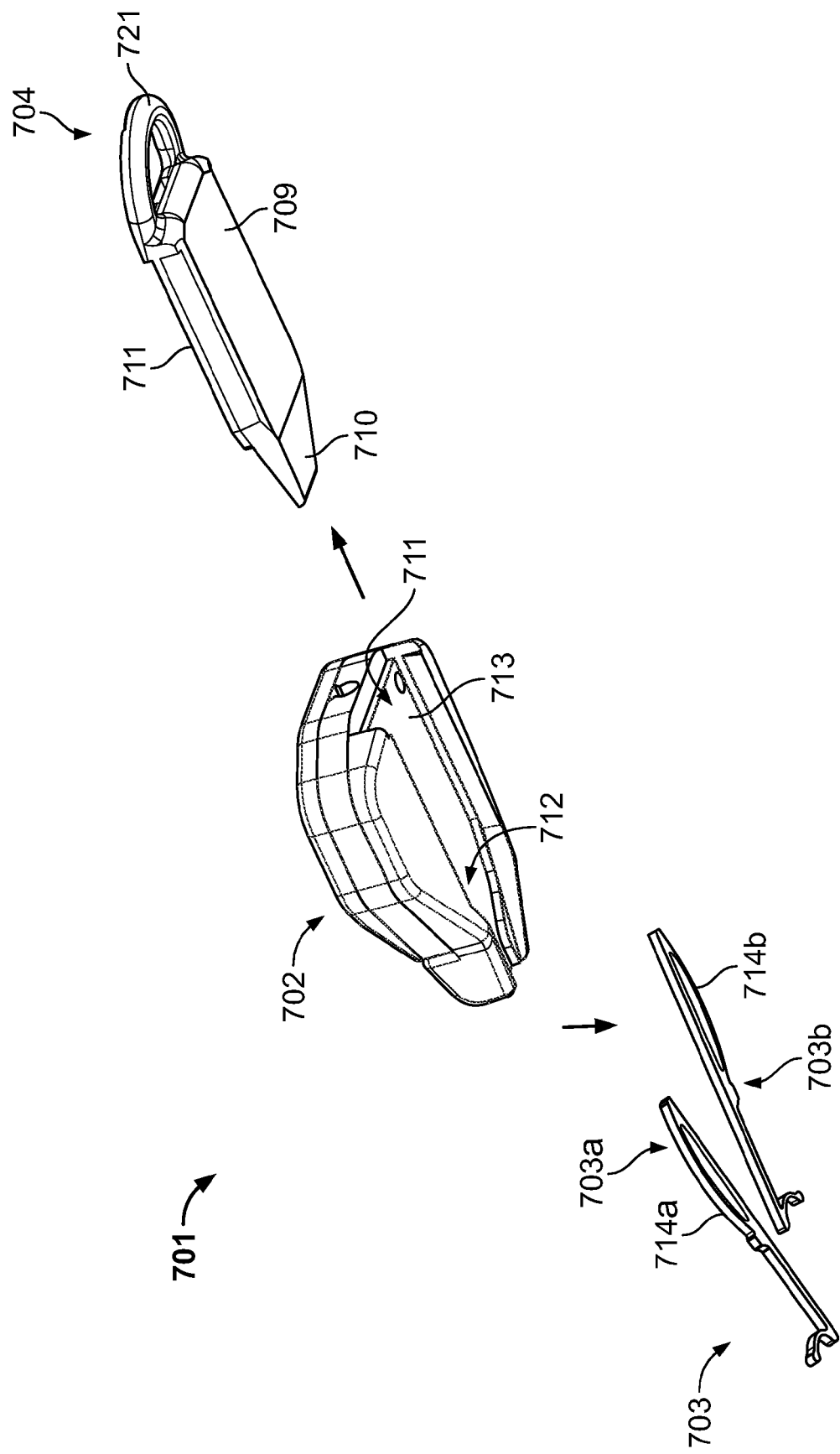
FIG. 9 is another perspective view of the anchor device of FIG. 7.

Referring now to FIGS. 7-9, some embodiments of an anchor system 700 may include an anchor device 701 that removably couples with a delivery device 750 to facilitate advancement of the anchors 703 toward a skin penetration point. As described in more detail below, the delivery device 750 can be configured to be readily grasped and manipulated by a user so as to firmly position the anchor device 701 proximate to the skin penetration point during deployment of the anchors 703 through the skin and into the subcutaneous region. Moreover, as described in more detail below, the anchor device 701 may include a release member 704 that facilitates prompt separation of the anchors 703 away from the retainer body 702, thereby permitting each anchors 703 to be removed from the skin penetration point independently of the other anchor(s) in a manner that reduces the likelihood of damage to the tissue surrounding the skin penetration point. As with previously described embodiments, the anchors 703 can be configured to be deployed into the subcutaneous layer of a patient's skin to secure a medical device (e.g., a catheter or the like) in place relative to a skin penetration point. For example, as shown in FIG. 8, the anchors 703*a-b* include anchor tines 728*a-b* that have a curved shape to abut the underside of the skin layer. The tines 728*a-b* can extend to free ends having atraumatic bulbs 729*a-b* that are configured to substantially reduce the likelihood of damage to the skin when the anchors 703*a-b* are deployed and withdrawn through the skin penetration point.

In this embodiment, the retainer body 701 includes locking pillars 705*a-b* that mate with apertures 727*a-b* on a retention member 725. Similar to previously described embodiments, the retention member 725 includes a channel 726 to secure a medical device (e.g., a catheter 20 as shown in FIGS. 10A-G) to the retention member 725. Furthermore, the locking pillars 705*a-b* can mate with a cap member 730 to compress the retention member 725 between the retainer body 702 and the cap member 730. The retention member 725 may comprise silicone or another flexible material so that the channel 726 can flexibly adjust to receive the catheter or another medical instrument therein. Accordingly, the apertures 727*a-b* can be forced over the corresponding pillars 705*a-b*, and thereafter the user may press the catheter 20 (FIG. 10C) into the channel 726. As the cap member 230 engages the pillars 705*a-b*, the compression of the retention member 725 causes the wall of the channel 726 to apply a frictional engagement to the outer surface of the catheter 20. Owing to the flexible nature of the retention member 725, the locking apertures 727*a-b* can stretch to fit over the locking pillars 705*a-b* during the mating process. The cap member 730 may comprise a more rigid material, such as ABS or the like, so as to apply the compressive force to the retention member 725. In such circumstances, the cap member 730 can include apertures 731*a-b* having notches, detents, or other structures that mate with corresponding structures on the locking pillars 705a-b so that the cap member 730 remains coupled to the retainer body 702.

Still referring to FIGS. 7-9, the retainer body 702 can include a guide channel 706 that provides guidance for the anchor device 701 during advancement toward the skin penetration point. For example, the guide channel 706 can be guided by the outer surface of the catheter 20 while the anchor device 701 is advanced toward the skin penetration point 32. The guide channel 706 can define a mouth that is delivered proximate to the skin penetration point, and thereafter the anchors 703 can be deployed to extend distally from the retainer body 701 and through the skin penetration point.

In some embodiments, the retainer body 701 can include a release member 704 that can be adjusted to cause the anchors 703 to decouple from the retainer body 702. Referring to FIG. 9, in this embodiment, the release member 704 can include a slidable body 709 releasably coupled to the retainer body 701. For example, the slidable body 709 movably engages an anchor channel 713 so that the release member can slide longitudinally away from the retainer body 702. The anchor channel 713 can be shaped such that a portion of its perimeter substantially matches a portion of the anchors 703a-b when they are conjoined. For example, a portion of each of the anchors 703a-b includes anchor handles 714a-b that can fit within a tapered portion 712 of the anchor channel 713. The anchors 703a-b can be arranged between the retainer body 702 and the release member 704 so as to shift from a non-deployed position (FIG. 10A) to a deployed position (refer to FIG. 10B). When in the non-deployed position, the anchors 703a-b are substantially contained between the anchor channel 713 and the slidably body 709 so that the tines 728a-b are at least partially flexed within the tapered portion 712. As described in more detail below, the anchors 703a-b can be forced to the deployed position in which the anchors 703a-b are shifted longitudinally out of the anchor channel 713 to extend distally from the retainer body 702. Similar to previously described embodiments, the anchors 703a-b may comprise a material that exhibits superelasticity when used in a patient's body.

As shown in FIG. 9, the slidable body 709 can includes a tapered tip 710 that facilitates assembly of the release member 704 with the retainer body. For example, the tapered tip 710 can be inserted into a proximal opening of the anchor channel 713 so that the slidably body 709 mates with guide rails in the anchor channel 713. When the release member 704 is fully mated with the retainer body 701, the tapered end 710 of the slidable body 709 mates with the tapered portion 712 of the channel 713. In some embodiments, the release member 704 can be releasably locked into position when it is fully mated with the retainer body 701, for example, through the use of a snap-fit connection or the like. The release member 704 can include one or more surface structures 711 that are configured to mate with the anchor handles 714a-b when the anchors are in the non-deployed position, the deployed position, or both. For example, the surface structures 711 may include one or more guide rails that permit the anchor handles 714a-b to shift distally inside the anchor channel 713 (e.g., from the non-deployed position to the deployed position) upon application of an actuator force, and the guide rails may thereafter inhibit movement of the anchor handles 714a-b in a reverse direction (e.g., thereby preventing accidental withdrawal of the anchors 703a-b after deployment).

Referring again to FIGS. 7-9, the release member 704 can include a gripping member 721 that facilitates separation of the sled slidably body 709 from the retainer body 702. In this embodiment, the gripping member 721 is in the form of a pull-ring that can be handle by a user's finger. In some implementations, a user can grasp the gripping member 721 and exert a longitudinal force in a proximal direction to overcome the snap-fit engagement and thereby free the release member 704 from the retainer body 702. As in more detail described below, when the release member 704 slides out of the retainer body 702 such that they become completely decoupled, the anchors 703a-b are free to fall out of the anchor channel 713 and thereby separate from the retainer body 702. It should be understood from the description herein that, in some embodiments, the anchor channel 713 can include stops that inhibit the anchors 703 from movement in the proximal direction when the release member 704 is being pulled from the retainer body 702. Thus, the anchors 703a-b can remain in the deployed configuration while the release member 704 is being pulled from the retainer body 702.

Referring to FIG. 7, some embodiments of the anchor system 700 can include the delivery device 750 that facilitates delivery and deployment of the anchor device 701. In this embodiment, the delivery device 750 includes a body 751 that can be formed of a rigid material and ergonomically shaped to allow a user to comfortably articulate the body 751 to skillfully deploy an anchor device. The body 751 includes a cavity 752 into which the anchor device 701 (e.g., the retainer body 702, retention member 725, and (optionally) cap 730) can be inserted and releasably coupled. In this embodiment, the cavity is configured to receive the retainer body 702 and the retention member 725, while the cap member 730 is employed after the retainer body 702 is separated from the delivery device 750. The anchor device 701 can couple into the cavity 752 with a snap-fit engagement, thereby allowing the anchor device 701 to be partially contained housed within the delivery device 750 until it is deployed. In some embodiments, the anchor device 790 can be retained in the cavity 752 through use of a locking mechanism such as a tab or detent that extends from the retainer body 701 and mates with a corresponding recess within the cavity 752 (not shown in FIG. 7). In some embodiments, the anchor device 701 can be housed completely within the cavity 752; in other embodiments, only a portion of the anchor device 701 is housed within the cavity 752.

The delivery device 750 can include a deployment piston 753 that acts upon a portion of the anchor device 701 when force is applied thereto. In the embodiment depicted in FIG. 7, the deployment piston 753 is in the form of a plunger (e.g., a syringe-like plunger) that can be forwardly advanced (e.g., under force from a user's thumb) to exert a deployment force on a portion of the anchor device 701. For example, a tongue 754 can be coupled to a distal portion of the deployment piston 753 to extend into the anchor channel 713 (FIG. 9) and act upon the anchors 703 therein. As described in more detail below, the tongue 754 can push upon the anchor handles 714a-b (FIG. 9) to force the anchors from the non-deployed position to the deployed position. Such an action can occur when the user forces the deployment piston 753 from an initial position to an intermediate position relative to the delivery device body 751.

Still referring to FIG. 7, in some embodiments, the deployment piston 753 may also serve to separate the anchor device 701 and the delivery device 750 after deployment of the anchors 703. For example, in the embodiment depicted in FIG. 7, the deployment piston 753 can include a pusher bar 755 to abut against the anchor device 701 (e.g., abuts against a rearward surface of the retainer body 702 or the retention member 725). As described in more detail below, the pusher bar 755 can force the anchor device 701 to separate from the cavity 752 of the delivery device 750 after the anchors 703 are deployed in the subcutaneous region. This separation action can occur when the user forces the deployment piston 753 from the intermediate position to a final distal position relative to the delivery device body 751.

In this embodiment, the tongue 754 and the pusher bar 755 are fixedly coupled to the deployment piston 753. The tongue 754 extends further in the distal direction than the pusher bar 755. As such, the tongue 754 can act to initiate deployment of the anchors 703 before the pusher bar 755 forces the anchor device to fully separate from the cavity 752. In other embodiments, the tongue 754 and the extension member 755 can be independently extendable. In such embodiments, the deployment piston 753 may have first and second piston surfaces (not shown in FIGS. 7-9) that independently engage the tongue 754 and the pusher bar 755 when the deployment piston 753 is forwardly advanced. Such an arrangement may be realized by allowing a portion of the deployment piston 753, including the first piston surface, to slide underneath, or proximal to the pusher bar 755 as the tongue 754 is being deployed.

Still referring to FIG. 7, some embodiments of the delivery device 750 includes a deployment gauge 766 that indicates a position of the deployment piston 753. In the embodiment of FIG. 7, the deployment gauge 766 has markings that visually indicates to the user the position of the deployment piston 753 (e.g., the initial position, the intermediate position, and the final distal position). Thus, the deployment gauge 766 can be used to determine the distance that the piston 753 should be advanced to deploy the anchors 703 and to detach the anchor system 701 from the delivery device. In some embodiments, marking indicia can be placed on the deployment piston 753 and the deployment gauge 766 is a window with marking indicia that allows a user to visually determine how far the deployment piston 753 has traveled in a longitudinal direction. In addition or in the alternative, the deployment gauge 766 may have an indicator in the form of an audible or tactile "click" for one or more of the initial position, the intermediate position, or the final distal position.

Referring now to FIGS. 10A-10G, some embodiments of the anchor system 700 can be implemented to secure a medical instrument at a selected location on a patient's body. For example, the anchor device 701 can be used in certain processes to secure the catheter 20 in a selected position relative to the skin penetration point 32 that is occupied by the catheter 20. Similar to the embodiments previously described herein, the anchor device 701 may properly secure the catheter 20 in this operative position without necessarily requiring sutures or adhesive tapes bonded to the skin.

Figure 10A:
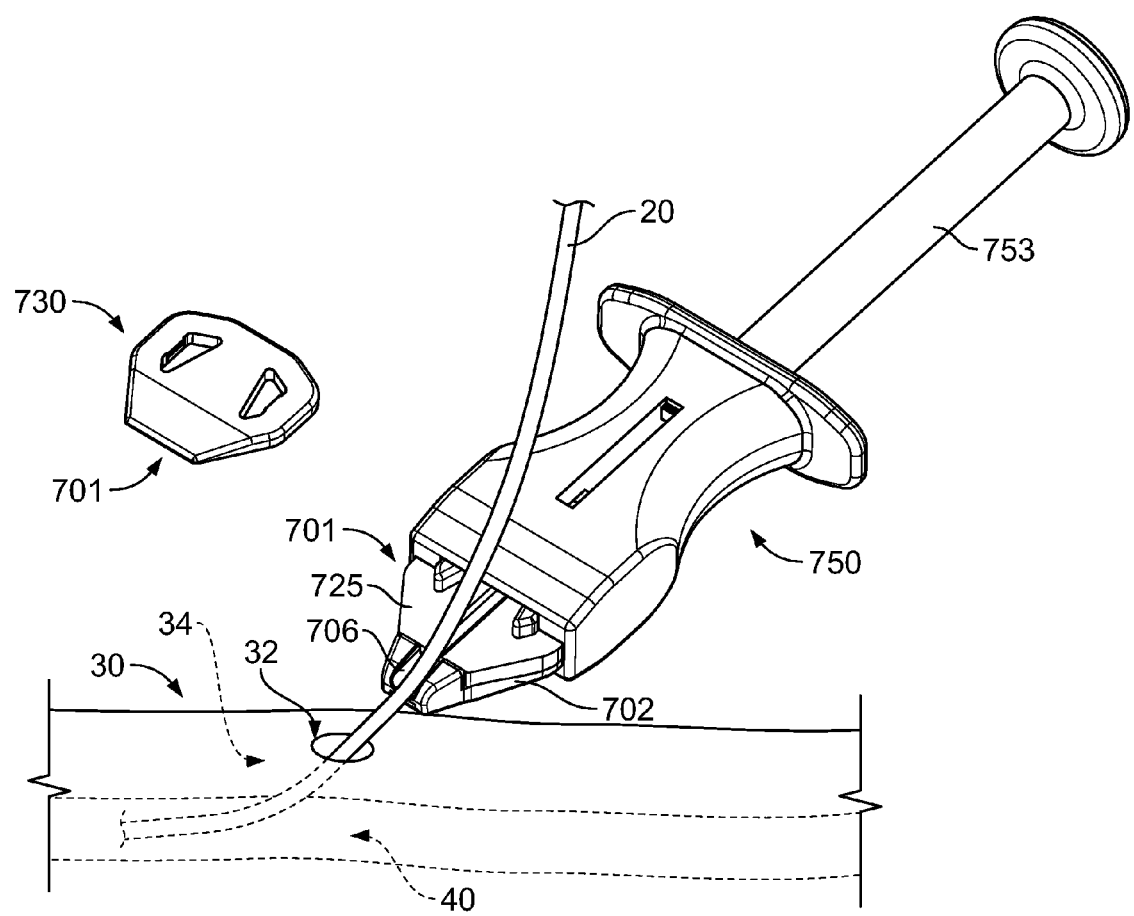
FIGS. 10A-G are perspective views of an exemplary implementation of the anchor device of FIG. 7.

As shown in FIG. 10A, a medical instrument (in this particular example, a catheter 20) has been delivered through a patient's skin 30, through the subcutaneous layer 34, and into a targeted vein 40. After the catheter 20 is advanced through the skin, the anchor device 701 can be directed along the catheter 20 and toward the skin penetration point 32 that is occupied by the catheter. As previously described, the skin penetration point 32 can be formed, for example, by an incision in the skin 30. In this embodiment, the anchor device 701 is advanced along the outer surface of the catheter 20 by handling the delivery device 750. The delivery device 750 can be configured so that a user can readily direct the anchor device 701 on a path toward the skin entry point 32. During such delivery, the guide channel 706 of the retainer body 702 can be guided along the outer surface of the catheter 20 until it is arranged proximate to the skin penetration point 32. When the delivery device 750 is used to direct the anchor device 701 to such a position, the user can prepare to shift the anchors 703 away from the non-deployed configuration. In this embodiment, the anchors 703 are substantially enclosed by the retainer body 702 (and the release member 704 (not shown in FIG. 10A) when in the non-deployed configuration.

Figure 10B:
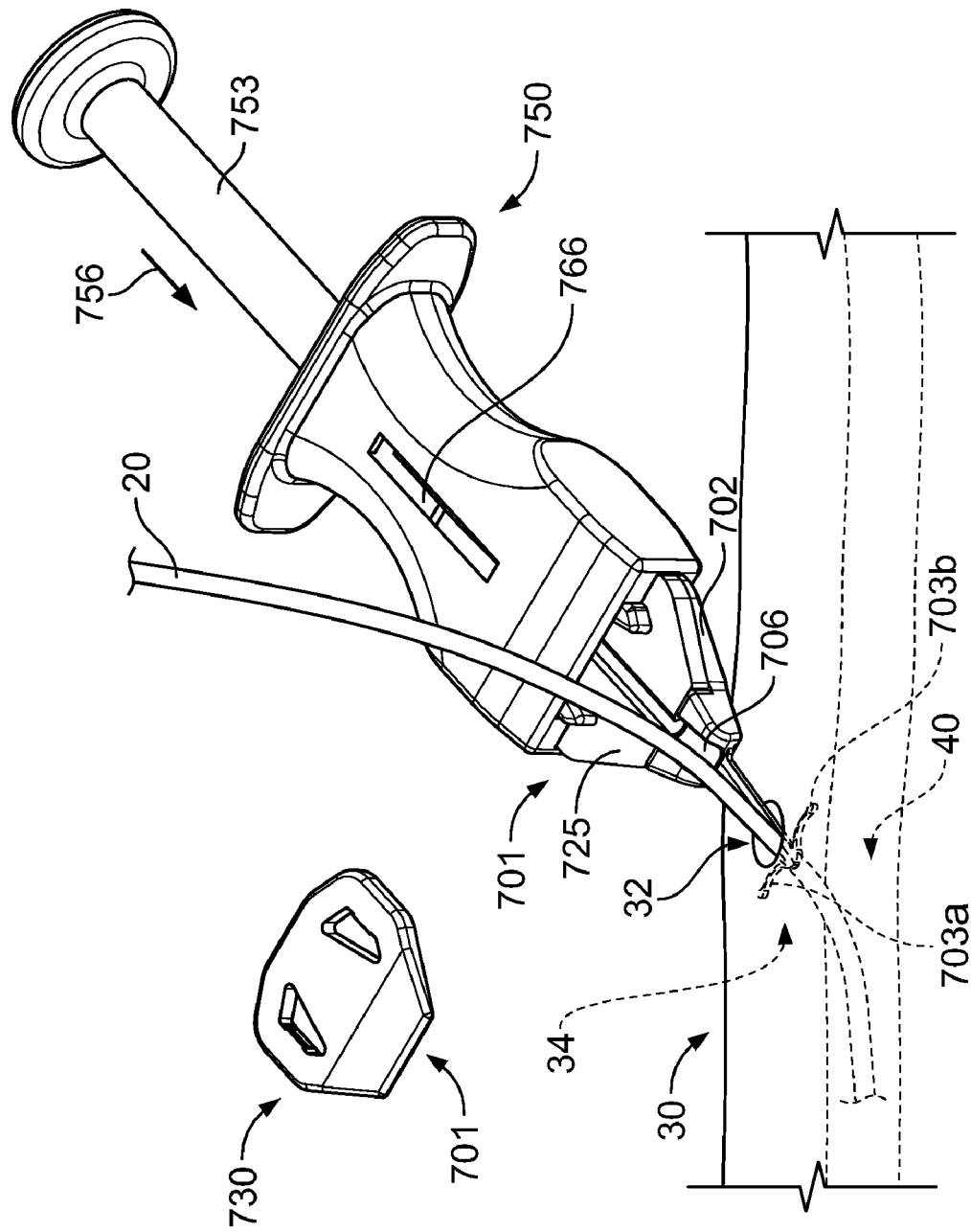

Referring to FIG. 10B, the user can deploy the anchors 703a-b by applying a deployment force 756 to the piston 753 of the delivery device 750. Such force 756 can be translated through the tongue 754 (FIG. 7) to the anchors 703a-b so that the anchors 703a-b move from the non-deployed configuration to the deployed configuration. The indicator 766 of the delivery device can show that the piston is actuated from the initial position to an intermediate position (to cause the anchors 703a-b to deploy). Because the delivery device 750 in this embodiment can be readily manipulated by the user during deployment, the user can maintain the position of the guide channel 706 while the anchors 703a-b are moved. As such, the delivery device 750 facilitates proper positioning of the anchor device 701 (e.g., in a position adjacent to the skin penetration point 32) while the anchors 703a-b are deployed. The anchors 703a-b can be fully deployed through the skin penetration point 32 and into the subcutaneous layer 34. When the anchors 703a-b reach the subcutaneous layer 34, the anchor tines 728a-b can flex outward to the deployed configuration. Accordingly, the tines 728a-b can secure the anchor device 701 in a selected position relative to the skin penetration point 32.

Figure 10C:
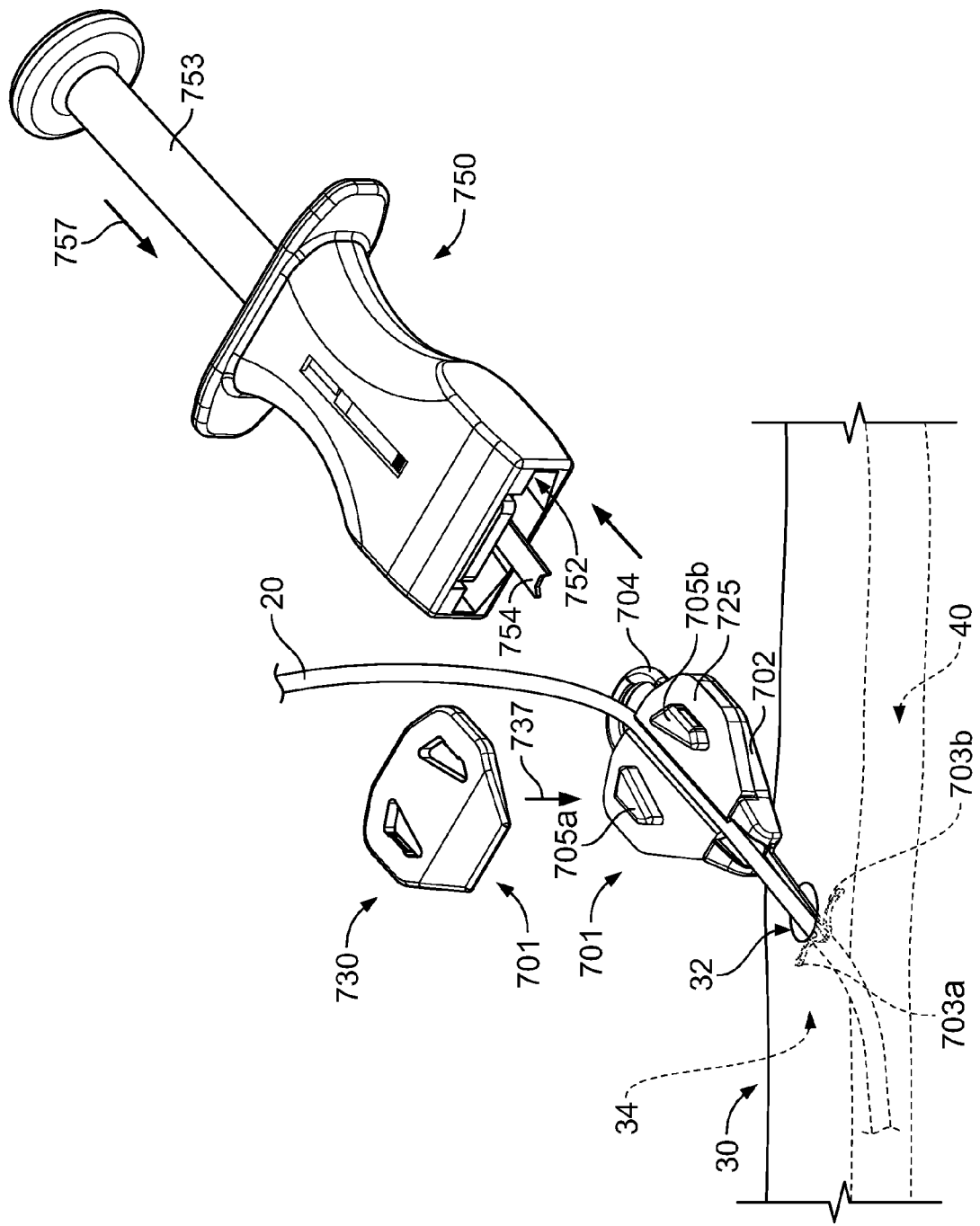

Referring to FIG. 10C, the anchor device 701 can be decoupled from the delivery device 750 by applying a detachment force 757 to the deployment piston 753. This force 757 can be translated through the pusher bar 755 (FIG. 7) to the anchor device 701 so that the anchor device 701 is dislodged from the cavity 752 of the delivery device 750. The indicator 766 of the delivery device may show that the piston is actuated from the intermediate position to the fully distal position (to cause separation from the anchor device 701). After the delivery device 701 is separated from the anchor device 701, the delivery device 750 can be discarded (e.g., thrown away in a trash bin, a recycle bin, or another discard bin). The catheter 20 can be pressed (e.g., with the user's fingers or another instrument) to fit into the full length of the channel 726 in the retention member 725, thereby coupling the catheter 20 to the anchor device 701. If the catheter was delivered to the targeted internal tissue site prior to deployment of the anchor device 701, then the catheter can be promptly inserted into the channel 726. If, however, the catheter 20 requires further adjustment after the anchor device 701 is deployed, then the catheter 20 can be further inserted (or retracted) to the targeted tissue site before the catheter 20 is fit into the channel 726. After the catheter 20 is engaged inside the channel 726 of the retention member 725, the cap member 730 can be pressed onto the locking pillars 705a-b to compress the retention member 725 around the catheter 20 (e.g., to create a frictional holding force).

Figure 10D:
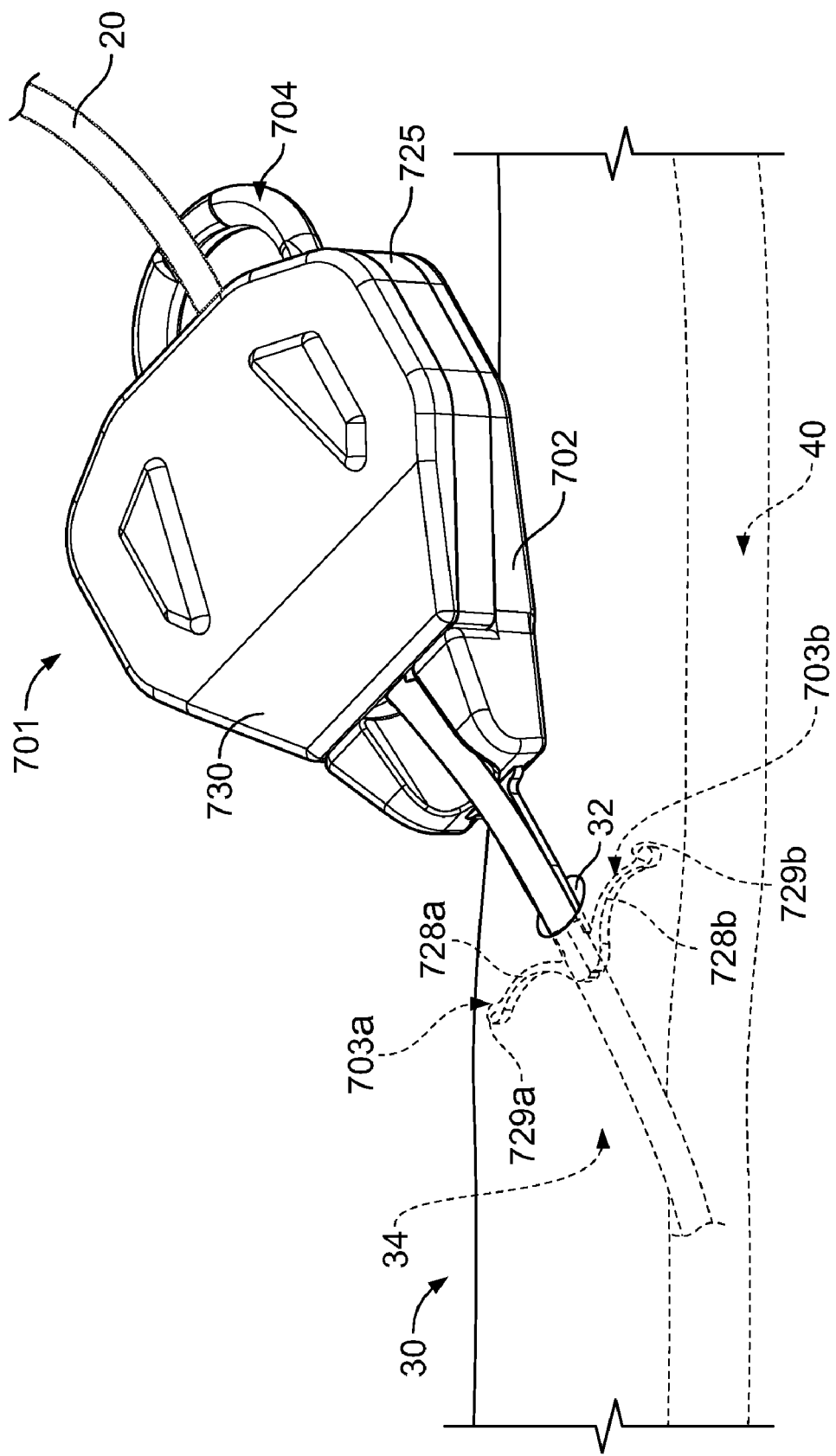

As shown in FIG. 10D, the anchor device 701 is assembled to secure the catheter 20 in a selected position relative to the skin penetration point 32. Thus, after the catheter 20 is delivered into the targeted vein 40 (or other bodily lumen) and after the anchors 703a-b are deployed in the subcutaneous region 34, the cap member 730 can mate with the retainer body 702 so that the retention member 725 lockingly engages the catheter 20 to secure its position relative to the retainer body 701. In this embodiment, the retention portion 725 can secure the catheter 20 relative to the skin penetration point 32 throughout the medical procedure in which the catheter 20 in employed. The configuration illustrated in FIG. 10D shows the anchor device 701 as it may be used to secure a patient's catheter 20 over a period of time, for example, for hours, one to seven days, or longer. As previously described, the anchors 703a-b may be designed such that the tines 728a-b include a curvature that abuts against the underside of the skin 30 in a manner that reduces the likelihood of the tines 728a-b puncturing through the underside of the skin 30. When the tines 728a-b are deployed in the subcutaneous region 34, the anchor device 701 can be secured to the patient without necessarily requiring sutures or adhesive tapes to bond the retainer body 702 to the skin 30.

Figure 10E:
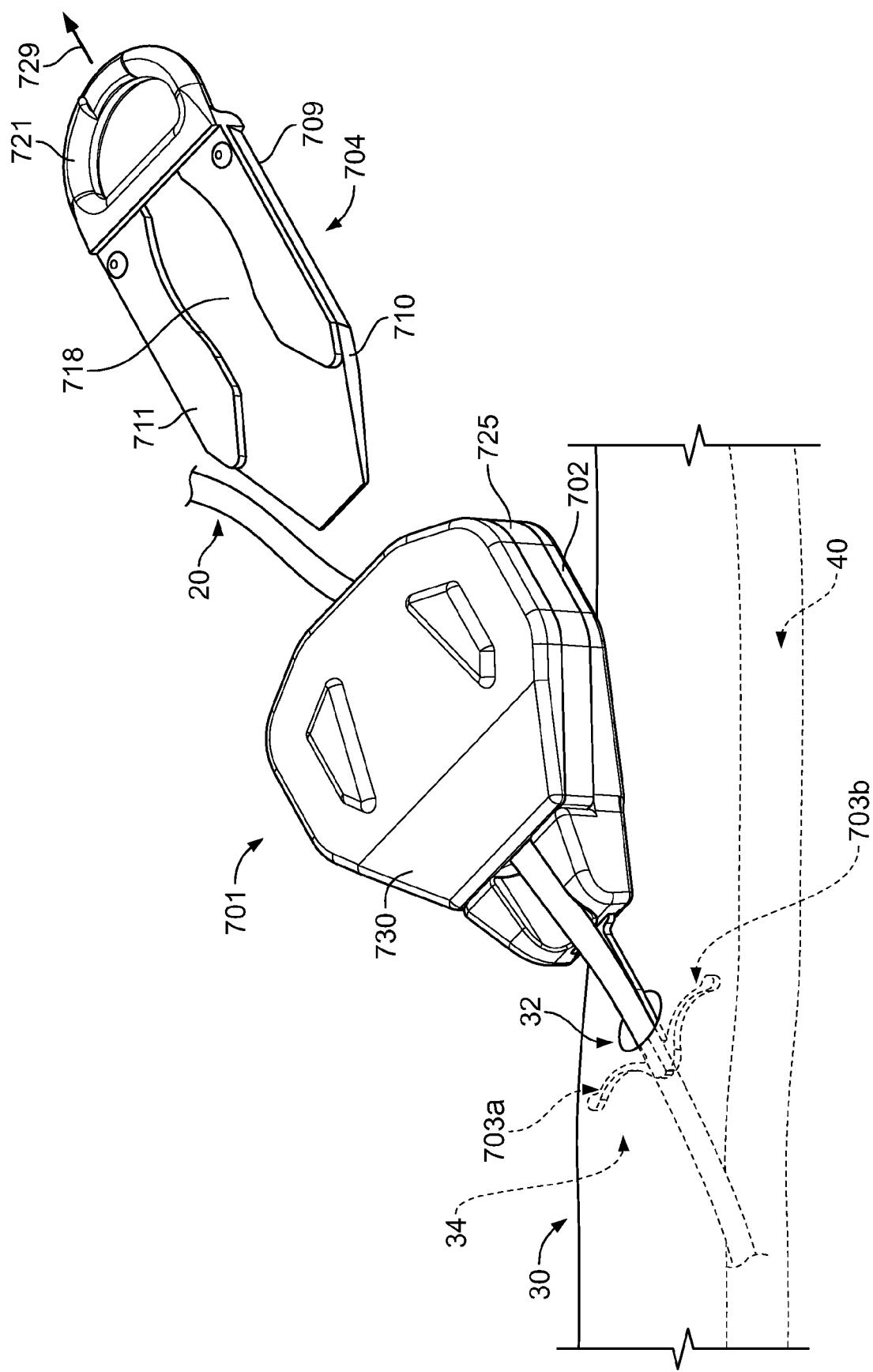
Figure 10F:
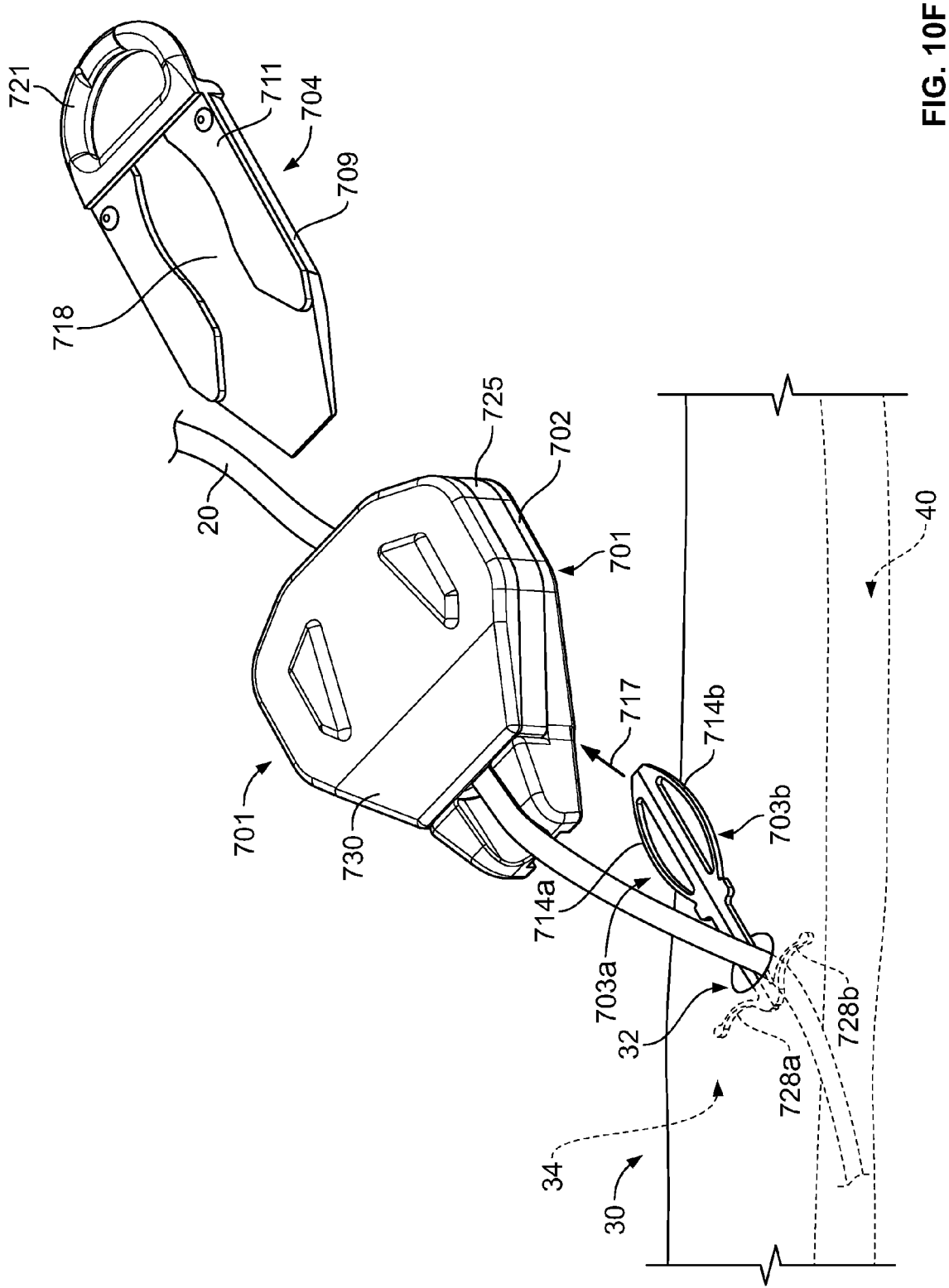
Figure 10G:
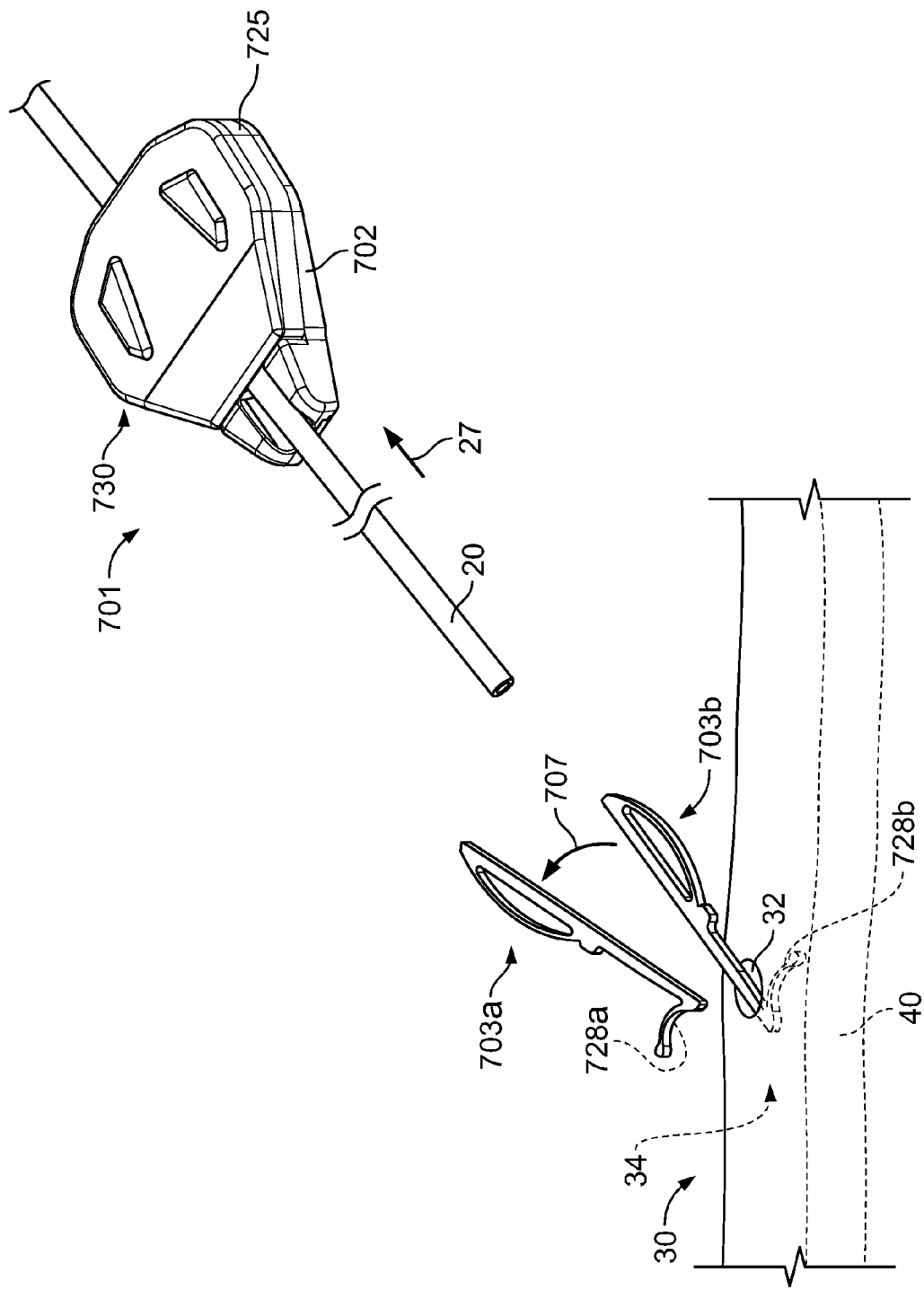

Referring to FIGS. 10E-G, the catheter 20 may be withdrawn from the patient (e.g., after the procedure) while the anchors 703a-b remain in the subcutaneous region 34. As such, in some embodiments, the anchors 703a-b can collectively penetrate into the subcutaneous layer 34 as part of the assembled device 701 9 refer to FIG. 10B), but may be separately and individually withdrawn from the penetration point 32 during the removal process (refer to FIG. 10G).

In the embodiment depicted in FIG. 10E, at least a portion of the anchor device 701 may be retracted with the catheter 20 when the catheter 20 is to be removed from the skin 30. For example, the release member 704 can be actuated to separate the anchors 703a-b from the retainer body 702, thereby permitting the retainer body 702, the retention member 725, and the cap member 730 to be withdrawn along with the catheter 20. As previously described, the release member 704 may include the slidable body 709 that can be pulled out of the anchor channel 713 (FIG. 9). For example, the user may apply a release force 729 to the ring 721, which causes the slidably body 709 to move in a proximal direction away from the retainer body 702. The surface structures 711 of the release member 704 can at least partially define a chamber 718 in which the anchor handles 714a-b (FIG. 9) reside. For example, when the anchors 703a-b are forced from the non-deployed configuration to the deployed configuration, the anchor handles 714a-b may shift from a position in a narrowed region of the chamber 718 to a position where the chamber widens (along the tapered tip 710). Accordingly, chamber 718 can be configured so that the release member 704 may be pulled rearwardly in the proximal direction without causing the anchors 703a-b to also withdraw in the proximal direction.

As shown in FIG. 10F, after the release member 704 is separated from the retainer body 702, the retainer body 702 (and the catheter 20 engaged therewith) can be withdrawn away from the anchors 703a-b. In this embodiment, the retainer body 702 can be lifted (refer to separation force 717) away from the anchors 703a-b-so that the anchor handles 714a-b are removed from the anchor channel 713 (FIG. 9). In such circumstances, the retainer body 702 and the retention member 725 can remain engaged with the catheter 20 during removal of the catheter from the skin penetration point 32. The anchors 703a-b can remain engaged with the skin 30 during the removal of the catheter 20. The catheter 20 can be fully retracted from the skin by application of a catheter withdrawal force 27. Because the retainer body 702 and the retention member 725 remain engaged with the catheter 20, these components can also be retracted away from the skin penetration point 32 and then discard along with the catheter 20.

As shown in FIG. 10G, after the anchors 703a-b are free from the retainer body 702, they can be individually maneuvered in such a way as to reduce the likelihood of damage to the skin tissue during removal. Similar to previously described embodiments, the anchors 703a-b may be separated and individually maneuvered so that one anchor 703a can be removed independent of the other anchor 703b. The anchors 703a-b can be separated from each other by, for example, applying a separation force 707 to the first anchor 703a, which urges the first anchor 703a apart from the second anchor 703b. Thereafter, the anchors 703a-b can be separately and individually removed from the skin penetration point 32 by shifting the anchor 703a in a direction that favors release of the tine 728a from the subcutaneous layer 34. Similar movements can be repeated for the remaining anchor 703b so to completely remove the anchors 703a-b in a manner that reduces the likelihood of damage to the surround skin tissue.

A number of embodiments have been described. Nevertheless, it will be understood that various modifications may be made without departing from the spirit and scope of the disclosed embodiments. For example, the anchor devices described herein can be configured to secure catheters that enter into bodily structures other than a vein 40. For example, the catheter 20 may be configured to pass into arteries, bodily lumens, and other cavities. In another example, the anchor device described herein can be configured to mate with medical instruments other than a catheter 20, such as endoscopes, illumination instruments, retraction instruments, or the like. Accordingly, other embodiments are within the scope of the following claims.

What is claimed is:

1. An anchor system for securing a medical instrument, comprising:
   a retainer body to couple to a catheter;
   a plurality of flexible anchors releasably coupled to the retainer body, each anchor comprising a flexible tine that is deployable in a subcutaneous region to secure the retainer body relative to a penetration point;
   an actuator that, when activated, moves the anchors from a non-deployed position to a deployed position in which the anchors flexible anchors extend distally from the retainer body and into the subcutaneous region; and
   a retention member coupled to the retainer body that directly engages an outer circumferential surface of the catheter when the retainer body couples to the catheter, wherein the retention member defines a gripping channel that at least partially surrounds the outer circumferential surface of the catheter when the retention member engages the catheter, wherein the gripping channel is at least partially defined by a wall comprising a silicone material to press against the outer circumferential surface of the catheter when the retention member engages the catheter.

2. The anchor system of claim 1, wherein when the anchors are separable from the retainer body when deployed in the subcutaneous region.

3. The anchor system of claim 2, wherein the plurality of anchors are releasably coupled together by the retainer body such that the anchors are collectively deployable into the subcutaneous region, and the anchors are separable from one another when the anchors are deployed in the subcutaneous region so that a first anchor is removable from the subcutaneous region independent of a second anchor.

4. The anchor system of claim 2, wherein the anchors are deployable to extend distally from the retainer body and into the penetration point occupied by the catheter when the retainer body couples to the catheter.

5. The anchor system of claim 1, wherein the actuator comprises a delivery device that is separable from the retainer body.

6. The anchor system of claim 5, wherein the delivery device comprises a movable shaft that is adjustable from a first position to a second position so as to move the anchors toward the deployed position and that is adjustable from the second position to a third position so as to decouple the retainer body from the delivery device.

7. The anchor system of claim 1, wherein the actuator is separable into a first body portion and a second body portion, and the plurality of anchors comprise a first anchor coupled to the first body portion and a second anchor coupled to the second body portion.

8. The anchor system of claim 7, wherein the actuator, when activated, shifts to engage a portion of the retainer body to secure the actuator in an activated position.

9. The anchor system of claim 1, wherein the plurality of anchors extend distally from the retainer body to deploy into the penetration point occupied by the catheter when the retainer body couples to the catheter.

10. The anchor system of claim 1, wherein the retention member is adjustable from an opened configuration to a closed configuration to engage the outer circumferential surface of the catheter.

11. The anchor system of claim 1, further comprising a guide channel that extends distally from the retention member and toward the plurality of anchors when the anchors are in the deployed position.

12. The anchor system of claim 1, wherein each of the anchors comprises a material that exhibits superelasticity.

13. The anchor system of claim 1, further comprising the catheter to couple with the retainer body.

14. An anchor system for securing a medical instrument, comprising:
 a retainer body to couple with a medical instrument, wherein a retention member coupled to the retainer body directly engages an outer surface of the medical instrument when the retainer body couples to the medical instrument, wherein the retention member defines an inwardly facing wall comprising a compliant gripping material that compresses against, and applies a holding force to, the outer surface of the medical instrument when the retention member engages the medical instrument;
 first and second anchors that are deployable through a skin penetration point and into subcutaneous region so as to secure the retainer body relative to the skin penetration point;
 a separable delivery device including an actuator that, when activated, moves the first and second anchors from a non-deployed position to a deployed position in which the anchors flexible anchors extend distally from the retainer body and into the subcutaneous region along an underside of a skin layer; and
 a release member that releasably couples the first and second anchors to the retainer body, the release member being adjustable from a first position to a second position in which the first and second anchors are decoupled from the retainer body.

15. The anchor system of claim 14, wherein the compliant gripping material of the inwardly facing wall of the retention member comprises a silicone material.

16. The anchor system of claim 14, wherein when the first and second anchors are releasable from the retainer body when deployed in the subcutaneous region.

17. The anchor system of claim 16, wherein the first and second anchors are releasably coupled together by the retainer body such that the first and second anchors are collectively deployable into the subcutaneous region, and the anchors are separable from one another when the anchors are deployed in the subcutaneous region so that the first anchor is removable from the subcutaneous region independent of the second anchor.

18. The anchor system of claim 17, wherein the anchors are deployable to extend distally from the retainer body and into the skin penetration point occupied by the medical instrument when the retainer body couples with the medical instrument.

19. The anchor system of claim 14, wherein the actuator of the delivery device is movable from a first position to a second position so as to move the first and second anchors toward the deployed position and is movable from the second position to a third position so as to cause separation of the retainer body from the delivery device.

20. The anchor system of claim 14, wherein each of the first and second anchors include a flexible curved tine that is engageable with bodily tissue along the underside of the skin layer when the anchor is deployed in the subcutaneous region.

21. The anchor system of claim 14, further comprising the medical instrument to couple with the retainer body.

22. The anchor system of claim 21, wherein the medical device comprises a catheter to extend distally through the same skin penetration point as the first and second anchors.

23. The anchor system of claim 14, wherein each of the first and second anchors include a flexible tine having a convexly curved longitudinal portion to abut an underside of a skin layer when deployed into the subcutaneous region.

24. The anchor system of claim 23, wherein the flexible curved tine of each of the first and second anchors extends to a free end having an atraumatic bulb.

25. An anchor system for securing a medical instrument, comprising:
 a retainer body to releasably couple to a catheter that occupies a skin penetration point, wherein the retainer body includes an adjustable retention member that directly engages an outer circumferential surface of the catheter when the retainer body releasably couples to the catheter; and
 first and second flexible anchors coupled to the retainer body and being configured to extend distally from a distal end of the retainer body, the first flexible anchor comprising a first curved tine and the second flexible anchor comprising a second curved tine, the first and second curved tines that is being deployable in a subcutaneous region adjacent to a skin layer to secure the retainer body relative to the skin penetration point, wherein the first and second curved tines are positioned distal to the distal end of the retainer body when deployable in the subcutaneous region adjacent to the skin layer,
 wherein the first and second anchors are retained in a non-deployed position prior to insertion through the skin penetration point and are actuatable to a deployed position in which the first and second flexible anchors extend distally from the distal end of the retainer body and through the skin penetration point occupied by the catheter.

26. The anchor system of claim 25, wherein when the first and second anchors are removable from the retainer body when deployed in the subcutaneous region.

27. The anchor system of claim 25, further comprising an actuator to move the first and second flexible anchors to the deployed position.

28. The anchor system of claim 25, wherein the first and second flexible anchors extend distally from the distal end of the retainer body to deploy into the skin penetration point occupied by the catheter while the retainer body resides fully external to the skin penetration point.

29. The anchor system of claim 25, wherein the retention member is adjustable from an opened configuration to a closed configuration to engage the outer circumferential surface of the catheter.

30. The anchor system of claim 29, wherein the retention member defines a gripping channel that at least partially surrounds the catheter when the retention member engages the catheter, wherein the gripping channel is at least partially defined by a wall comprising a soft gripping flexible material to flexibly press against, and apply a frictional holding force to, the outer circumferential surface of the catheter when the retention member engages the catheter.

31. The anchor system of claim 30, further comprising a guide channel that extends distally from the retention member and toward the first and second anchors when the anchors are in the deployed position.

32. The anchor system of claim 31, further comprising the catheter to releasably couple with the retainer body.

33. The anchor system of claim 31, wherein each of the first and second curved tines having a convexly curved portion that extends longitudinally toward a non-sharp free end, wherein the convexly curved portion is oriented to abut an underside of the skin layer when deployed into the subcutaneous region.

* * * * *

UNITED STATES PATENT AND TRADEMARK OFFICE
CERTIFICATE OF CORRECTION

| | | |
|---|---|---|
| PATENT NO. | : 8,038,653 B2 | Page 1 of 1 |
| APPLICATION NO. | : 12/174306 | |
| DATED | : October 18, 2011 | |
| INVENTOR(S) | : Michael S. Rosenberg | |

It is certified that error appears in the above-identified patent and that said Letters Patent is hereby corrected as shown below:

Column 19, line 9 (Claim 30), after "gripping" please delete "flexible";

Column 20, line 5 (Claim 32), please delete "Claim 31" and insert --Claim 25-- therefor;

Column 20, line 7 (Claim 33), please delete "Claim 31" and insert --Claim 25-- therefor.

Signed and Sealed this
Thirteenth Day of March, 2012

David J. Kappos
*Director of the United States Patent and Trademark Office*